United States Patent
Iaccino et al.

(10) Patent No.: US 9,896,396 B2
(45) Date of Patent: Feb. 20, 2018

(54) PROCESS AND SYSTEM FOR MAKING CYCLOPENTADIENE AND/OR DICYCLOPENTADIENE

(71) Applicant: ExxonMobil Chemical Patents Inc., Baytown, TX (US)

(72) Inventors: Larry L. Iaccino, Seabrook, TX (US); Kevin C. P. Leung, Beijing (CN)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/288,354

(22) Filed: Oct. 7, 2016

(65) Prior Publication Data

US 2017/0121244 A1    May 4, 2017

Related U.S. Application Data

(60) Provisional application No. 62/250,708, filed on Nov. 4, 2015.

(51) Int. Cl.
*C07C 5/327* (2006.01)
*C07C 5/32* (2006.01)
(Continued)

(52) U.S. Cl.
CPC .......... *C07C 5/373* (2013.01); *B01J 8/02* (2013.01); *B01J 8/0278* (2013.01); *B01J 29/44* (2013.01);
(Continued)

(58) Field of Classification Search
CPC ............ C07C 5/327; C07C 5/32; C07C 5/333
(Continued)

(56) References Cited

U.S. PATENT DOCUMENTS

| | | |
|---|---|---|
| 2,438,400 A | 3/1948 | Hetzel et al. |
| 2,438,401 A | 3/1948 | Kennedy et al. |

(Continued)

FOREIGN PATENT DOCUMENTS

| | | |
|---|---|---|
| CN | 102951985 A | 3/2013 |
| DE | 2535809 | 3/1976 |

(Continued)

OTHER PUBLICATIONS

U.S. Appl. No. 62/250,678, filed Nov. 4, 2015, Iaccino, et al.
(Continued)

*Primary Examiner* — Thuan D Dang

(57) ABSTRACT

Processes and systems for making cyclopentadiene and/or dicyclopentadiene include converting acyclic C5 hydrocarbon(s) into CPD in a first reactor to obtain a first reactor hydrocarbon effluent, which is processed in an eductor to obtain an eductor effluent at higher total pressure than atmospheric pressure, separating the eductor effluent in a separator such as compression train to obtain a C5-rich fraction comprising CPD, dimerizing the C5-rich fraction in a second reactor to obtain a product effluent comprising DCPD, which is separated to obtain a DCPD-rich fraction. Multiple-stage of dimerization and separation steps can be optionally used to obtain multiple DCPD-rich fractions of various degrees of purity and quantity. C5-rich fractions from various stages of the process may be recycled to the first reactor, or converted into mogas components after selective hydrogenation. C5-rich fractions and mogas components may be optionally separated to produce value-adding chemicals.

24 Claims, 3 Drawing Sheets

(51) Int. Cl.

| | | |
|---|---|---|
| C07C 5/333 | (2006.01) | |
| C07C 5/373 | (2006.01) | |
| B01J 8/02 | (2006.01) | |
| B01J 29/44 | (2006.01) | |
| C07C 2/76 | (2006.01) | |
| C07C 5/03 | (2006.01) | |
| C07C 7/04 | (2006.01) | |
| C07C 4/22 | (2006.01) | |
| C07C 2/40 | (2006.01) | |
| C07C 2/52 | (2006.01) | |
| C01B 3/26 | (2006.01) | |

(52) U.S. Cl.
 CPC .............. *C01B 3/26* (2013.01); *C07C 2/403* (2013.01); *C07C 2/52* (2013.01); *C07C 2/76* (2013.01); *C07C 4/22* (2013.01); *C07C 5/03* (2013.01); *C07C 5/333* (2013.01); *C07C 7/04* (2013.01); *B01J 2208/02* (2013.01); *C01B 2203/043* (2013.01); *C01B 2203/0405* (2013.01); *C01B 2203/046* (2013.01); *C01B 2203/107* (2013.01); *C01B 2203/1058* (2013.01); *C01B 2203/1064* (2013.01); *C07C 2101/10* (2013.01); *C07C 2103/68* (2013.01); *C07C 2529/44* (2013.01); *C07C 2601/10* (2017.05); *C07C 2603/68* (2017.05); *Y02P 20/582* (2015.11)

(58) Field of Classification Search
 USPC ........................................ 585/365, 366, 369
 See application file for complete search history.

(56) References Cited

U.S. PATENT DOCUMENTS

| | | |
|---|---|---|
| 2,438,404 A | 3/1948 | Hetzel et al. |
| 2,982,798 A | 5/1961 | Hachmuth et al. |
| 3,593,968 A | 7/1971 | Geddes |
| 3,674,883 A | 7/1972 | Schleppinghoff et al. |
| 4,121,908 A | 10/1978 | Raab et al. |
| 4,140,587 A | 2/1979 | Paret et al. |
| 4,444,697 A | 4/1984 | Gater et al. |
| 4,886,926 A | 12/1989 | Dessau et al. |
| 5,324,486 A | 6/1994 | Russo |
| 5,633,421 A | 5/1997 | Iezzi et al. |
| 2003/0100809 A1 | 5/2003 | Tian et al. |
| 2006/0151122 A1 | 7/2006 | Hines, Jr. et al. |
| 2007/0197484 A1 | 8/2007 | Bakshi |
| 2007/0197848 A1 | 8/2007 | Baksi |

FOREIGN PATENT DOCUMENTS

| | | |
|---|---|---|
| JP | 62010025 | 1/1987 |
| JP | 2001247490 | 9/2001 |
| RU | 2463284 | 10/2012 |
| WO | 89/04818 | 6/1989 |
| WO | 02/36529 A | 5/2002 |

OTHER PUBLICATIONS

U.S. Appl. No. 62/250,692, filed Nov. 4, 2015, Iaccino, et al.
U.S. Appl. No. 62/250,702, filed Nov. 4, 2015, Iaccino, et al.
U.S. Appl. No. 62/250,708, filed Nov. 4, 2015, Iaccino, et al.
Fel'dblyum, V.S., et al. "*Cyclization and Dehydrocyclization of $C_5$ Hydrocarbons over Platinum Nanocatalysts and in the Presence of Hydrogen Sulfide,*" Doklady Chemistry, 2009, vol. 424, Part 2, pp. 27-30.

PROCESS AND SYSTEM FOR MAKING CYCLOPENTADIENE AND/OR DICYCLOPENTADIENE

CROSS-REFERENCE TO RELATED APPLICATIONS

This invention claims priority to and the benefit of U.S. Ser. No. 62/250,708, filed Nov. 4, 2015. This application relates to: U.S. Ser. No. 62/250,678, filed Nov. 4, 2015; U.S. Ser. No. 62/250,692, filed Nov. 4, 2015; and U.S. Ser. No. 62/250,702, filed Nov. 4, 2015.

FIELD OF THE INVENTION

The present invention relates to processes and systems for making cyclic C5s including cyclopentadiene and/or dicyclopentadiene. In particular, the present invention relates to processes and systems for making cyclopentadiene and dicyclopentadiene from acyclic C5 hydrocarbons.

BACKGROUND OF THE INVENTION

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. Typically, cyclopentadiene is produced as a minor byproduct in liquid fed steam cracking (e.g., naphtha and heavier feed) processes. As steam cracking processes shift to using lighter feed (e.g., ethane and propane feed), less CPD is produced while demand for CPD continues to rise. Cyclopentane and cyclopentene also have high value as solvents while cyclopentene may be used as a monomer to produce polymers and as a starting material for other high value chemicals.

Consequently, there is a need for on-purpose CPD production, i.e., CPD produced as a primary product from a feedstock as opposed to CPD produced as a minor byproduct. U.S. Pat. No. 5,633,421 generally discloses a process for dehydrogenating C2-C5 paraffins to obtain corresponding olefins. Similarly, U.S. Pat. No. 2,982,798 generally discloses a process for dehydrogenating aliphatic hydrocarbons containing 3 to 6, inclusive, carbon atoms. However, neither U.S. Pat. No. 5,633,421 nor U.S. Pat. No. 2,982,798 discloses production of CPD from acyclic C5 hydrocarbons, which are desirable as feedstock because they are plentiful and low cost. Further, many challenges exist in designing an on-purpose CPD production process. For example, the reaction converting C5 hydrocarbons to CPD is extremely endothermic and is favored by low pressure and high temperature but significant cracking of n-pentane and other C5 hydrocarbons can occur at relatively low temperature (e.g., 450° C.-500° C.). Other challenges include loss of catalyst activity due to coking during the production process and further processing is needed to remove coke from the catalyst, and the inability to use oxygen-containing gas to directly provide heat input to the reactor without damaging the catalyst.

From the perspective of storage and shipping, DCPD is easier to handle than CPD as a feed material for subsequent chemical syntheses. DCPD and CPD are fungible in many applications. In certain applications DCPD is preferably used directly in lieu of CPD. For other applications where CPD is needed, DCPD can be thermally depolymerized (a/k/a cracked) via retro-Diels-Alder reaction to CPD at the point of use.

Conventional processes for making CPD typically produce C5 hydrocarbon stream(s) comprising CPD at a modest concentration, acyclic diolefins at significant concentrations, and mono olefins. Because many of the C5 species have close boiling points, form azeotropes, and are reactive at distillation temperatures, CPD recovery from the product mixture via conventional distillation is not industrially feasible. In conventional recovery schemes, CPD is recovered from other C5 hydrocarbons utilizing dimerization process(es) which causes CPD to undergo Diels-Alder reaction to produce DCPD that can easily be separated from the C5 hydrocarbons by conventional distillation. Unfortunately, CPD can also react with other diolefins present in the stream to produce co-dimers, which contaminate the DCPD. Furthermore, reactions involving higher-order oligomers also occur at moderate to high temperatures. These side reactions produce undesirable co-dimers and higher-order oligomers, which necessitate more downstream processing steps, such as repeated, multi-step cracking and dimerization, to produce DCPD with sufficient purity required for many applications. Such processes are expensive, low in yield, and can be prone to fouling. In addition, air and oxygen ingress into the CPD reactor and downstream processes and equipment, which can occur when the first reactor operates at below-atmospheric pressure, is highly undesirable. However, thermodynamic equilibrium constraints suppress conversion of acyclic C5 hydrocarbons to CPD when CPD and/or hydrogen partial pressures are elevated.

Therefore, there is a need for processes and systems for the production of CPD and/or DCPD that address the above described challenges.

SUMMARY OF THE INVENTION

It has been found that by combining a catalytic acyclic C5 hydrocarbon conversion process where production of CPD is favored over acyclic diolefins, an eductor system (comprising one or multiple eductors operated in parallel) for increasing the overall pressure of the product stream while maintaining acceptably low partial pressures of CPD and/or hydrogen, and an effective separation process thereafter minimizing the Diels-Alder reactions between CPD and acyclic diolefins, CPD can be produced at a high yield, from which high-purity DCPD can be produced.

A first aspect of the present invention relates to a process for making CPD and/or DCPD comprising: (I) feeding a C5 feedstock comprising at least one acyclic C5 hydrocarbon into a first reactor; (II) contacting the at least one acyclic C5 hydrocarbon with a catalyst under conversion conditions to obtain a first reactor hydrocarbon effluent from an outlet of the first reactor comprising: C5 components including CPD and acyclic diolefins; light components including hydrogen and C1-C4 hydrocarbons; one-ring aromatics; and multiple-ring aromatics; (III) feeding at least a portion of the first reactor hydrocarbon effluent to a suction chamber of an eductor; (IV) injecting a stream of a motive fluid through a nozzle into the suction chamber; (V) obtaining an eductor effluent from an exit of the eductor comprising the motive fluid and CPD; wherein: the overall pressure of the first reactor effluent at the outlet of the first reactor is lower than the overall pressure of the eductor effluent at the exit of the eductor; and the temperature of the first reactor hydrocarbon effluent at the outlet of the first reactor is higher than the temperature of the eductor effluent at the exit of the eductor.

A second aspect of the present invention relates to a system for making CPD and/or DCPD, comprising: (A) a first reactor configured to receive a C5 feedstock comprising at least one acyclic C5 hydrocarbon, an optional hydrogen co-feedstock and an optional C1-C4 hydrocarbon co-feedstock; (B) a catalyst loaded inside the first reactor capable of catalyzing the conversion of the acyclic C5 hydrocarbon under conversion conditions to produce a first reactor hydrocarbon effluent comprising: C5 components including CPD and acyclic diolefins; light components including hydrogen and C1-C4 hydrocarbons; one-ring aromatics; and multiple-ring aromatics; (C) an eductor configured to receive at least a portion of the first reactor hydrocarbon effluent and a stream of a motive fluid, and to produce an eductor effluent comprising the motive fluid and CPD, wherein the eductor effluent at the exit of the eductor has (i) a higher overall pressure than the first reactor hydrocarbon effluent at the outlet of the first reactor and (ii) a temperature lower than the first reactor hydrocarbon effluent at the outlet of the first reactor; and (D) a first separation sub-system configured to receive at least a portion of the eductor effluent and to produce (i) a first C5-rich fraction comprising CPD and depleted of hydrogen and C1-C4 hydrocarbons; (ii) a light components-rich fraction comprising hydrogen and C1-C4 hydrocarbons; and (iii) a first multiple-ring aromatics-rich fraction.

DETAILED DESCRIPTION OF THE INVENTION

Figure 1:
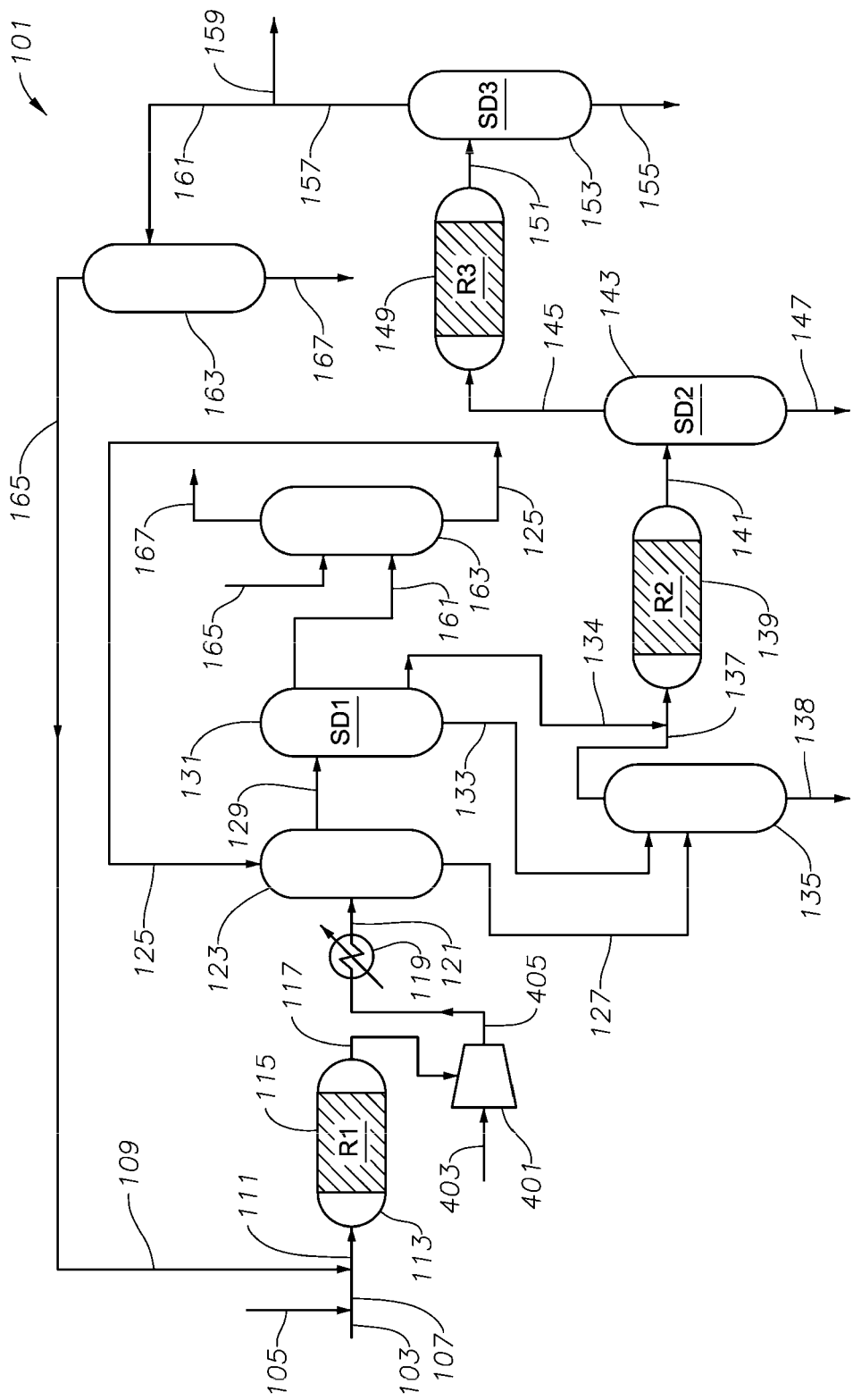
FIG. 1 is a schematic illustration of an exemplary process and system for making CPD and/or DCPD of the present invention.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each of the steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for making the measurement.

All numbers and references to the Periodic Table of Elements are based on the new notation as set out in Chemical and Engineering News, 63(5), 27 (1985), unless otherwise specified.

Definitions

For the purpose of this specification and appended claims, the following terms are defined.

The term "cyclic C5" or "cC5" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclic" includes, but is not limited to, linear and branched saturates and non-saturates.

The term "alkyl" includes saturated hydrocarbyl groups, which can be linear, branched, cyclic, or a combination of cyclic, linear and/or branched linear.

The term "aromatic" means a planar cyclic hydrocarbyl with conjugated double bonds, such as benzene. As used herein, the term aromatic encompasses compounds containing one or more aromatic rings, including, but not limited to, benzene, toluene and xylene and polynuclear aromatics (PNAs) which include, but are not limited to, naphthalene, anthracene, chrysene, and their alkylated versions. The term "C6+ aromatics" includes compounds based upon an aromatic ring having six or more ring atoms, including, but not limited to, benzene, toluene and xylene and polynuclear aromatics (PNAs) which include, but are not limited to, naphthalene, anthracene, chrysene, and their alkylated versions.

The term "BTX" includes, but is not limited to, a mixture of benzene, toluene, and xylene (ortho and/or meta and/or para).

As used herein, the term "rich," when used to describe a component in a given mixture or stream produced from a predecessor mixture or stream, means that the component is present at a non-negligible concentration in the given mixture or stream that is higher than its concentration in the predecessor mixture or stream. Thus, a C5-rich fraction produced from a predecessor stream is a fraction comprising C5 hydrocarbons at a non-negligible concentration that is higher than the concentration of C5 hydrocarbons in the predecessor stream.

As used herein, the term "depleted," when used to describe a component in a given mixture or stream produced from a predecessor mixture or stream, means that the component is present at a concentration (which can be negligible) in the given mixture or stream that is lower than its concentration in the predecessor mixture or stream. Thus, a hydrogen-depleted fraction produced from a predecessor stream is a fraction comprising hydrogen at a concentration (which can be negligible) that is lower than the concentration of hydrogen in the predecessor stream.

As used herein, "wt %" means percentage by weight, "vol %" means percentage by volume, and "mol %" means percentage by mole. All ranges expressed herein should include both end points as two specific embodiments unless specified or indicated to the contrary.

An "upper stream" as used herein may be at the very top or the side of a vessel such as a fractionation column or a reactor, with or without an additional stream above it. Preferably, an upper stream is drawn at a location in the vicinity of the top of the column. Preferably, an upper stream is drawn at a location above at least one feed. A "lower stream" as used herein is at a location lower than the upper stream, which may be at the very bottom or the side of a vessel, and if at the side, with or without an additional stream below it. Preferably, a lower stream is drawn at a location in the vicinity of the bottom of the column. Preferably, a lower stream is drawn at a location below at least one feed. As used herein, a "middle stream" is a stream between an upper stream and a lower stream.

The term "light hydrocarbons" means hydrocarbons comprising 1 to 4 carbon atoms in their molecule structures. The term "light components" means hydrogen and hydrocarbons comprising 1 to 4 carbon atoms in their molecule structures. The term "hydrogen" means molecular $H_2$.

The term "normal boiling point" means boiling point under a pressure of 101 kilopascal. The terms "vapor" and "gas" are both inclusive to mean a phase that is entirely vapor, entirely gas and mixtures of gas and vapor.

As used herein, the term "essentially free of" means comprising at a concentration not higher than 1 wt %, e.g., ≤0.8 wt %, ≤0.6 wt %, ≤0.5 wt %, ≤0.1 wt %, ≤0.01 wt %, or even ≤0.001 wt %.

The term "mogas" means a mixture of organic compounds suitable as fuel for use in gasoline internal combustion engine.

The term "coke" includes, but is not limited to, a low hydrogen content hydrocarbon that is adsorbed on the catalyst composition.

The term "Cn" means hydrocarbon(s) having n carbon atom(s) per molecule, wherein n is a positive integer. Thus, a C5 hydrocarbon feedstock, therefore, comprises one or more hydrocarbon, saturated or unsaturated, having 5 carbon atoms per molecule, such as n-pentane, 2-methyl-butane, 2,2-dimethylpentane, 1-pentene, 2-pentene, 2-methyl-2-butene, 3-methyl-2-butene, 1,3-pentadiene, 1,4-pentadiene, 2-methyl-1,3-butadiene, cyclopentane, cyclopentene, and the like.

The term "Cn+" means hydrocarbon(s) having at least n carbon atom(s) per molecule.

The term "Cn−" means hydrocarbon(s) having no more than n carbon atom(s) per molecule.

The term "hydrocarbon" means a class of compounds containing hydrogen bonded to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "C5 feedstock" includes a feedstock containing n-pentane, such as a feedstock which is predominately normal pentane (n-pentane) and/or isopentane (also referred to as methylbutane), with smaller fractions of cyclopentane and/or neopentane (also referred to as 2,2-dimethylpropane).

The term "one-ring aromatics" means aromatic compounds having one benzene ring in the molecular structures thereof and includes alkylated versions thereof such as toluene, xylenes, and ethylbenzene.

The term "multiple-ring aromatics" means aromatic compounds having two or more aromatic rings in the molecular structures thereof and includes alkylated versions thereof.

The term "Group 10 metal" means an element in Group 10 of the Periodic Table and includes Ni, Pd and Pt.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

The term "Group 11 metal" means an element in Group 11 of the Periodic Table and includes, but is not limited to, Cu, Ag, Au, and a mixture of two or more thereof.

The term "constraint index" is defined in U.S. Pat. No. 3,972,832 and U.S. Pat. No. 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline material".

As used herein, the term "carbon selectivity" means the moles of carbon in the respective cyclic C5, CPD, C1, and C2-4 formed divided by total moles of carbon in the C5 feedstock converted. The term "carbon selectivity to cyclic C5 of at least 30%" means that 30 moles of carbon in the cyclic C5 is formed per 100 moles of carbon in the C5 feedstock (such as n-pentane) converted.

As used herein, the term "conversion" means the moles of carbon in the acyclic C5 hydrocarbon(s) that is converted to a product. The term "conversion of at least 70% of said acyclic C5 hydrocarbon(s) to a product" means that at least 70% of the moles of said acyclic C5 hydrocarbon(s) was converted to a product.

As used herein, the term "ferrosilicate" means an iron-containing microporous crystalline structure that contains iron in the framework structure and/or in the channel system.

The term "alkylated naphthalene(s)" includes monoalkyl, dialkyl, trialkyl, and tetraalkyl naphthalenes.

The C5 Feedstock

A C5 feedstock comprising acyclic C5 hydrocarbon(s) useful herein is obtainable from crude oil or natural gas condensate, can include virgin C5, and can include cracked C5 (in various degrees of unsaturation: alkenes, dialkenes, alkynes) produced by refining and to chemical processes, such as fluid catalytic cracking (FCC), reforming, hydrocracking, hydrotreating, coking, and steam cracking.

In one or more embodiments, the C5 feedstock useful in the process of this invention comprises pentane, pentene, pentadiene and mixtures of two or more thereof. Preferably, in one or more embodiments, the C5 feedstock comprises at least about 50 wt %, or 60 wt %, or 75 wt %, or 90 wt % saturated acyclic C5 hydrocarbon(s), ideally n-pentane, or in the range from about 50 wt % to about 100 wt % saturated acyclic C5 hydrocarbon(s), ideally n-pentane. Preferably, 2-methylbutane is present at less than 10 wt %.

The C5 feedstock optionally does not comprise C6 aromatic compounds, such as benzene. Preferably C6 aromatic compounds are present at less than 5 wt %, or less than 1 wt %, or less than 0.01 wt %, or even 0 wt %.

The C5 feedstock optionally does not comprise toluene and/or one or more of the xylenes (ortho, meta and para). Preferably, toluene and xylenes (ortho, meta and para) are present in the C5 feedstock at less than 5 wt %, preferably less than 1 wt %, preferably present at less than 0.01 wt %, preferably at 0 wt %.

The C5 feedstock optionally does not comprise C6+ aromatic compounds, preferably C6+ aromatic compounds are present at less than 5 wt %, preferably less than 1 wt %, preferably present at less than 0.01 wt %, preferably at 0 wt %.

The C5 feedstock optionally does not comprise C6+ compounds, preferably C6+ compounds are present at less than 5 wt %, preferably less than 1 wt %, preferably present at less than 0.01 wt %, preferably at 0 wt %, preferably any C6+ aromatic compounds are present at less than 5 wt %, preferably less than 1 wt %, preferably present at less than 0.01 wt %, preferably at 0 wt %.

In the present invention, the acyclic C5 hydrocarbon(s) contained in the C5 feedstock is fed into a first reactor loaded with a catalyst, where the acyclic C5 hydrocarbons contact the catalyst under conversion conditions, whereupon at least a portion of the acyclic C5 hydrocarbon(s) molecules are converted into CPD molecules, and a reaction product containing CPD and, optionally, other cyclic hydrocarbons (e.g., C5 cyclic hydrocarbons such as cyclopentane and cyclopentene) exits the first reactor as a first reactor hydrocarbon effluent. Preferably, a hydrogen co-feedstock comprising hydrogen and, optionally, light hydrocarbons, such as C1-C4 hydrocarbons, is also fed into the first reactor. Preferably, at least a portion of the hydrogen co-feedstock is admixed with at least a portion, preferably the entirety, of the C5 feedstock prior to being fed into the first reactor. The presence of hydrogen in the feed mixture at the inlet location, where the feed first comes into contact with the catalyst, prevents or reduces the formation of coke on the catalyst particles. The catalyst composition, which is described in greater detail below, may comprise a microporous crystalline metallosilicate, preferably having a constraint index in the range of less than 12, a Group 10 metal in combination with a Group 1 alkali metal and/or a Group 2 alkaline earth metal; and, optionally, a Group 11 metal. The catalyst can be made by using a method described in greater detail below.

The first reactor can be a plug flow reactor or other reactor configurations. The catalyst can be loaded as a fixed bed, a catalyst particle fluid, and the like. As used herein, the term "reactor" refers to any vessel(s) in which a chemical reaction occurs. Reactor includes both distinct reactors as well as reaction zones within a single reactor apparatus and as applicable, reactions zones across multiple reactors. In other words and as is common, a single reactor may have multiple reaction zones. Where the description refers to a first and second reactor, the person of ordinary skill in the art will readily recognize such reference includes two reactors as well as a single reactor having first and second reaction zones. Likewise, a first reactor hydrocarbon effluent and a second reactor effluent will be recognized to include the effluent from the first reaction zone and the second reaction zone of a single reactor, respectively.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where $U_{mf}$ is minimum fluidizing velocity, $U_{mb}$ is minimum bubbling velocity, $U_c$ is the velocity at which fluctuation in pressure peaks, and $U_{tr}$ is transport velocity. These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010, which are incorporated by reference herein.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$, in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein the term "cascaded fluid-beds" means a series arrangement of individual fluid-beds such that there can be a gradient in gas and/or solid property (such as, temperature, gas or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated and/or separated from the product stream and then returned back to the reactor.

As used herein the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, 2nd Edition, Butterworth-Heinemann, Boston, 1991 and Walas, S. M., Chapter 6 of *Chemical Process Equipment*, Revised 2nd Edition, Butterworth-Heinemann, Boston, 2010. A fluidized bed reactor, such as a circulating fluidized bed reactor, may be operated as a riser reactor.

As used herein, the term "co-current" refers to a flow of two streams (e.g., stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

Acyclic C5 Conversion Process

The process for the conversion of an acyclic C5 hydrocarbon to a product comprising cyclic C5 compounds comprises contacting the C5 feedstock and, optionally, hydrogen under acyclic C5 conversion conditions in the presence of one or more catalyst compositions, including but not limited to the catalyst compositions described herein, to form said product. The product of the process for conversion of an acyclic C5 feedstock comprises cyclic C5 compounds. The cyclic C5 compounds can comprise one or more of cyclopentane, cyclopentene, cyclopentadiene, and includes mixtures thereof.

In one or more embodiments, the acyclic C5 conversion conditions include at least a temperature, a partial pressure, and a weight hourly space velocity (WHSV). The temperature is in the range of about 400° C. to about 700° C., or in the range from about 450° C. to about 650° C., preferably, in the range from about 500° C. to about 600° C. The partial pressure is in the range of about 3 to about 100 psi (21 to 689 kilopascal), or in the range from about 3 to about 50 psi (21 to 345 kilopascal), preferably, in the range from about 3 to about 20 psi (21 to 138 kilopascal). The weight hourly space velocity is in the range from about 1 to about 50 $hr^{-1}$, or in the range from about 1 to about 20 $hr^{-1}$. Such conditions include a molar ratio of the optional hydrogen co-feed to the acyclic C5 hydrocarbon in the range of about 0 to 3, or in the range from about 0.5 to about 2. Such conditions may also include co-feed C1-C4 hydrocarbons with the acyclic C5 feed.

In one or more embodiments, this invention relates to a process for conversion of n-pentane to cyclopentadiene comprising the steps of contacting n-pentane and, optionally, hydrogen (if present, typically $H_2$ is present at a molar ratio of hydrogen to n-pentane of 0.01 to 3.0) with one or more catalyst compositions, including but not limited to the catalyst compositions described herein, to form cyclopentadiene at a temperature of 400° C. to 700° C., a partial pressure of 3 to about 100 psia, and a weight hourly space velocity of 1 to about 50 $hr^{-1}$.

In the presence of the catalyst, a number of desired and undesirable side reactions may take place. The net effect of the reactions is the production of hydrogen and the increase of total volume (assuming constant total pressure). One particularly desired overall reaction (i.e., intermediate reaction steps are not shown) is:

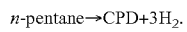
n-pentane→CPD+3H₂.

Additional overall reactions include, but are not limited to:

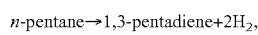
n-pentane→1,3-pentadiene+2H₂,

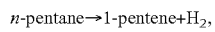
n-pentane→1-pentene+H₂, n-pentane→2-pentene+H₂,

n-pentane→2-methyl-2-butene+H₂,

n-pentane→cyclopentane+H₂,

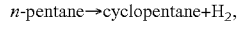
cyclopentane→cyclopentene+H₂, or

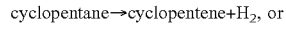
cyclopentene→CPD+H₂.

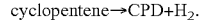
Fluids inside the first reactor are essentially in gas phase. At the outlet of the first reactor, a first reactor hydrocarbon effluent, preferably in gas phase, is obtained. The first reactor hydrocarbon effluent may comprise a mixture of the following hydrocarbons, among others: heavy components comprising more than 8 carbon atoms such as multiple-ring aromatics; C8, C7, and C6 hydrocarbons such as one-ring aromatics; CPD (the desired product); unreacted C5 feedstock material such as n-pentane; C5 by-products such as pentenes (1-pentene, 2-pentene, e.g.), pentadienes (1,3-pentadiene, 1,4-pentadiene, e.g.), cyclopentane, cyclopentene, 2-methylbutane, 2-methyl-1-butene, 3-methyl-1-butene, 2-methyl-1,3-butadiene, 2,2-dimethylpropane, and the like; C4 by-products such as butane, 1-butene, 2-butene, 1,3- butadiene, 2-methylpropane, 2-methyl-1-propene, and the like; C3 by-products such as propane, propene, and the like; C2 by-products such as ethane and ethene, methane, and hydrogen.

The first reactor hydrocarbon effluent may comprise CPD at a concentration of C(CPD)1 wt %, based on the total weight of the C5 hydrocarbons in the first reactor hydrocarbon effluent; and a1≤C(CPD)1≤a2, where a1 and a2 can be, independently, 15, 16, 18, 20, 22, 24, 25, 26, 28, 30, 32, 34, 35, 36, 38, 40, 45, 50, 55, 60, 65, 70, 75, 80, or 85 as long as a1<a2.

The first reactor hydrocarbon effluent may comprise acyclic diolefins at a total concentration of C(ADO)1 wt %, based on the total weight of the C5 hydrocarbons in the first reactor hydrocarbon effluent; and b1≤C(ADO)1≤b2, where b1 and b2 can be, independently, 20, 18, 16, 15, 14, 12, 10, 8, 6, 5, 4, 3, 2, 1, or 0.5, as long as b1<b2. Preferably, 0.5≤C(ADO)≤10. Preferably, the acyclic diolefins comprise 1,3-pentadiene at a concentration of C(PTD)1 wt %, based on the total weight of C5 components in the first reactor hydrocarbon effluent; and c1≤C(PTD)1≤c2, where c1 and c2 can be, independently, 20, 18, 16, 15, 14, 12, 10, 8, 6, 5, 4, 3, 2, 1, 0.5, or 0.3, as long as c1<c2.

As a result of the use of the catalyst and the choice of reaction conditions in the first reactor, a high CPD to acyclic diolefin molar ratio in the first reactor hydrocarbon effluent can be achieved such that C(CPD)1/C(ADO)1≥1.5, preferably 1.6, 1.8, 2.0, 2.2, 2.4, 2.5, 2.6, 2.8, 3.0, 3.2, 3.4, 3.5, 3.6, 3.8, 4.0, 5.0, 6.0, 8.0, 10, 12, 14, 15, 16, 18, or 20. The high ratio of C(CPD)1/C(ADO)1 significantly reduces CPD loss as a result of Diels-Alder reactions between CPD and acyclic dienes in subsequent processing steps, and therefore, allows the processes of the present invention to achieve high DCPD yield and high DCPD purity for the subsequently produced DCPD fractions.

Desirably, the total absolute pressure and temperature of the first reactor hydrocarbon effluent should be maintained at levels such that the dimerization of CPD to form DCPD is substantially avoided, and the Diels-Alder reactions between CPD and acyclic dienes are substantially inhibited.

Because the overall conversion from acyclic C5 hydrocarbons to CPD and hydrogen results in substantial volume increase (assuming constant total system pressure), a low partial pressure of CPD and/or a low partial pressure of hydrogen in the reaction mixture favors the conversion of acyclic C5 hydrocarbons. The total partial pressure of C5 hydrocarbons and hydrogen in the first reactor effluent at the outlet is desired to be lower than atmospheric pressure. Thus, where insufficient co-feedstock of a C1-C4 hydrocarbon or other co-feedstock is introduced into the first reactor, the total overall pressure of the first reactor effluent is desirably sub-atmospheric, in order to achieve a level of satisfactory conversion from acyclic C5 hydrocarbons to CPD. However, direct separation of a sub-atmospheric stream has the disadvantage of potential oxygen/air ingress into the system, resulting in oxidation of CPD and other hydrocarbons and formation of undesirable species in the system. Thus, it is desirable that the first reactor hydrocarbon effluent is processed to a higher total pressure before separation thereof. Eductor systems, described in greater detail below, can be used for that purpose.

Catalyst Composition

Catalyst compositions useful herein include microporous crystalline metallosilicates, such as crystalline aluminosilicates, crystalline ferrosilicates, or other metal containing crystalline silicates (such as those where the metal or metal containing compound is dispersed within the crystalline silicate structure and may or may not be a part of the crystalline framework). Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU where one or more metals from groups 8, 11, and 13 of the Periodic Table of the Elements (preferably one or more of Fe, Cu, Ag, Au, B, Al, Ga, and or In) are incorporated in the crystal structure during synthesis or impregnated post crystallization. It is recognized that a metallosilicate may have one or more metals present and, for example, a material may be referred to as a ferrosilicate, but it will most likely still contain small amounts of aluminum.

The microporous crystalline metallosilicates preferably have a constraint index of less than 12, alternately from 1 to 12, alternately from 3 to 12. Aluminosilicates useful herein have a constraint index of less than 12, such as 1 to 12, alternately 3 to 12, and include, but are not limited to Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the microporous crystalline aluminosilicate has a constraint index of about 3 to about 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573, ZSM-50 is described in U.S. Pat. No. 4,640,829, and ZSM-57 is described in U.S. Pat. No. 4,873,067. ZSM-58 is described in U.S. Pat. No. 4,698,217. Constraint index and a method for its determination are described in U.S. Pat. No. 4,016,218. The entire contents of each of the aforementioned patents are incorporated herein by reference.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697) and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the microporous crystalline metallosilicate has an Si/M molar ratio greater than about 3, or greater than about 25, or greater than about 50, or greater than about 100, or greater than about 400, or in the range from about 100 to about 2,000, or from about 100 to about 1,500, or from about 50 to about 2,000, or from about 50 to 1,200.

In one or more embodiments, the microporous crystalline aluminosilicate has an SiO2/Al2O3 molar ratio greater than about 3, or greater than about 25, or greater than about 50, or greater than about 100, or greater than 400, or in the range from about 100 to about 400, for from about 100 to about 500, or from about 25 to about 2,000, or from about 50 to about 1,500, or from about 100 to 1,200 from about 100 to 1000.

In another embodiment of the invention, the microporous crystalline metallosilicate (such as an aluminosilicate) is combined with a Group 10 metal or metal compound, and, optionally, one, two, three, or more Group 1, 2, or 11 metals or metal compounds.

In one or more embodiments, the Group 10 metal includes, or is selected from the group consisting of, Ni, Pd and Pt, preferably Pt. The Group 10 metal content of said catalyst composition is at least 0.005 wt %, based on the weight of the catalyst composition. In one or more embodiments, the Group 10 content is in the range from about 0.005 wt % to about 10 wt %, or from about 0.005 wt % up to about 1.5 wt %, based on the weight of the catalyst to composition.

In one or more embodiments, the Group 1 alkali metal includes, or is selected from the group consisting of, Li, Na, K, Rb, Cs, and mixtures of two or more thereof, preferably Na.

In one or more embodiments, the Group 2 alkaline earth metal is selected from the group consisting of Be, Mg, Ca, Sr, Ba, and mixtures of two or more thereof.

In one or more embodiments, the Group 1 alkali metal is present as an oxide and the metal is selected from the group consisting of Li, Na, K, Rb, Cs, and mixtures of two or more thereof. In one or more embodiments, the Group 2 alkaline earth metal is present as an oxide and the metal is selected from the group consisting of Be, magnesium, calcium, Sr, Ba, and mixtures of two or more thereof. In one or more embodiments, the Group 1 alkali metal is present as an oxide and the metal is selected from the group consisting of Li, Na, K, Rb, Cs, and mixtures of two or more thereof; and the Group 2 alkaline earth metal is present as an oxide and the metal is selected from the group consisting of Be, magnesium, calcium, Sr, Ba, and mixtures of two or more thereof.

In one or more embodiments, the Group 11 metal includes, or is selected from the group consisting of, silver, gold, copper, preferably silver or copper. The Group 11 metal content of said catalyst composition is at least 0.005 wt %, based on the weight of the catalyst composition. In one or more embodiments, the Group 11 content is in the range from about 0.005 wt % to about 10 wt %, or from about 0.005 wt % up to about 1.5 wt %, based on the weight of the catalyst composition.

In one or more embodiments, the catalyst composition has an Alpha Value (as measured prior to the addition of the Group 10 metal, preferably platinum) of less than 25, alternately less than 15, alternately from 1 to 25, alternately from 1.1 to 15.

In one or more embodiments of aluminosilicates the molar ratio of said Group 1 alkali metal to Al is at least about 0.5, or from at least about 0.5 up to about 3, preferably at least about 1, more preferably at least about 2.

In one or more embodiments of aluminosilicates, the molar ratio of said Group 2 alkaline earth metal to Al is at least about 0.5, or from at least about 0.5 up to about 3, preferably at least about 1, more preferably at least about 2.

In one or more embodiments, the molar ratio of said Group 11 metal to Group 10 metal is at least 0.1, or from at least about 0.1 up to about 10, preferably at least about 0.5, more preferably at least about 1. In one or more embodiments, the Group 11 alkaline to earth metal is present as an oxide and the metal is selected from the group consisting of gold, silver, and copper, and mixtures of two or more thereof.

Preferably, catalyst compositions useful herein are employed at conversion conditions, including a temperature in the range of from 400 to 800° C., a pressure in the range of from 10 to 1,000 kilopascal absolute, and a WHSV in the range of 1 to 100 hr$^{-1}$. In one or more embodiments, the use of the catalyst compositions of this invention provides a conversion of at least about 60%, or at least about 75%, or at least about 80%, or in the range from about 60% to about 80%, of said acyclic C5 feedstock under acyclic C5 conversion conditions of an n-pentane containing feedstock with equimolar $H_2$, a temperature in the range of about 550° C. to about 600° C., an n-pentane partial pressure between 3 and 10 psia, and an n-pentane weight hourly space velocity of 10 to 20 hr$^{-1}$.

In one or more embodiments, the use of any one of the catalyst compositions of this invention provides a carbon selectivity to cyclic C5 compounds of at least about 30%, or at least about 40%, or at least about 50%, or in the range from about 30% to about 80%, under acyclic C5 conversion conditions including an n-pentane feedstock with equimolar $H_2$, a temperature in the range of about 550° C. to about 600° C., an n-pentane partial pressure between 3 and 10 psia, and an n-pentane weight hourly space velocity between 10 and 20 hr$^{-1}$.

In one or more embodiments, the use of any one of the catalyst compositions of this invention provides a carbon selectivity to cyclopentadiene of at least about 30%, or at least about 40%, or at least about 50%, or in the range from about 30% to about 80%, under acyclic C5 conversion conditions including an n-pentane feedstock with equimolar $H_2$, a temperature in the range of about 550° C. to about 600° C., an n-pentane partial pressure between 3 and 10 psia, and an n-pentane weight hourly space velocity between 10 and 20 hr$^{-1}$.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of microcrystalline material and matrix may vary widely, with the crystal content ranging from about 1 to about 90 wt % and more usually, particularly when the composite is prepared in the form of beads, extrudates, pills, oil drop formed particles, spray dried particles, etc., in the range of about 2 to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques including high pressure hydrogen treatment and combustion of coke on the catalyst compositions with an oxygen-containing gas.

Useful catalyst compositions comprise a crystalline aluminosilicate or ferrosilicate, which is optionally combined with one, two or more additional metals or metal compounds. Preferred combinations include:
1) a crystalline aluminosilicate (such as ZSM-5 or Zeolite L) combined with a Group 10 metal (such as Pt), a Group 1 alkali metal (such as sodium or potassium) and/or a Group 2 alkaline earth metal;

2) a crystalline aluminosilicate (such as ZSM-5 or Zeolite L) combined with a Group 10 metal (such as Pt) and a Group 1 alkali metal (such as sodium or potassium);
3) a crystalline aluminosilicate (such as a ferrosilicate or an iron treated ZSM-5) combined with a Group 10 metal (such as Pt), a Group 1 alkali metal (such as sodium or potassium);
4) a crystalline aluminosilicate (Zeolite L) combined with a Group 10 metal (such as Pt) and a Group 1 alkali metal (such as potassium); and
5) a crystalline aluminosilicate (such as ZSM-5) combined with a Group 10 metal (such as Pt), a Group 1 alkali metal (such as sodium), and a Group 11 metal (such as silver or copper).

Another useful catalyst composition is a group 10 metal (such as Ni, Pd and Pt, preferably Pt) supported on silica (e.g., silicon dioxide) modified by a Group 1 alkali metal silicate (such as a Li, Na, K, Rb, and/or Cs silicates) and/or a Group 2 alkaline earth metal silicate (such as e, Mg, Ca, Sr, and/or Ba silicates), preferably potassium silicate, sodium silicate, calcium silicate and/or magnesium silicate, preferably potassium silicate and/or sodium silicate. The Group 10 metal content of the catalyst composition is at least 0.005 wt %, based on the weight of the catalyst composition, preferably, in the range from about 0.005 wt % to about 10 wt %, or from about 0.005 wt % up to about 1.5 wt %, based on the weight of the catalyst composition. The silica ($SiO_2$) may be any silica typically used as catalyst support such as those marketed under the tradenames of DAVISIL 646 (Sigma Aldrich), DAVISON 952, DAVISON 948 or DAVISON 955 (Davison Chemical Division of W.R. Grace and Company).

For more information on useful catalyst compositions, please see filed applications:
1) U.S. Ser. No. 62/250,675, filed Nov. 4, 2015;
2) U.S. Ser. No. 62/250,681, filed Nov. 4, 2015;
3) U.S. Ser. No. 62/250,688, filed Nov. 4, 2015;
4) U.S. Ser. No. 62/250,695, filed Nov. 4, 2015; and
5) U.S. Ser. No. 62/250,689, filed Nov. 4, 2015;
which are incorporated herein by reference.

The Eductor

Figure 3:
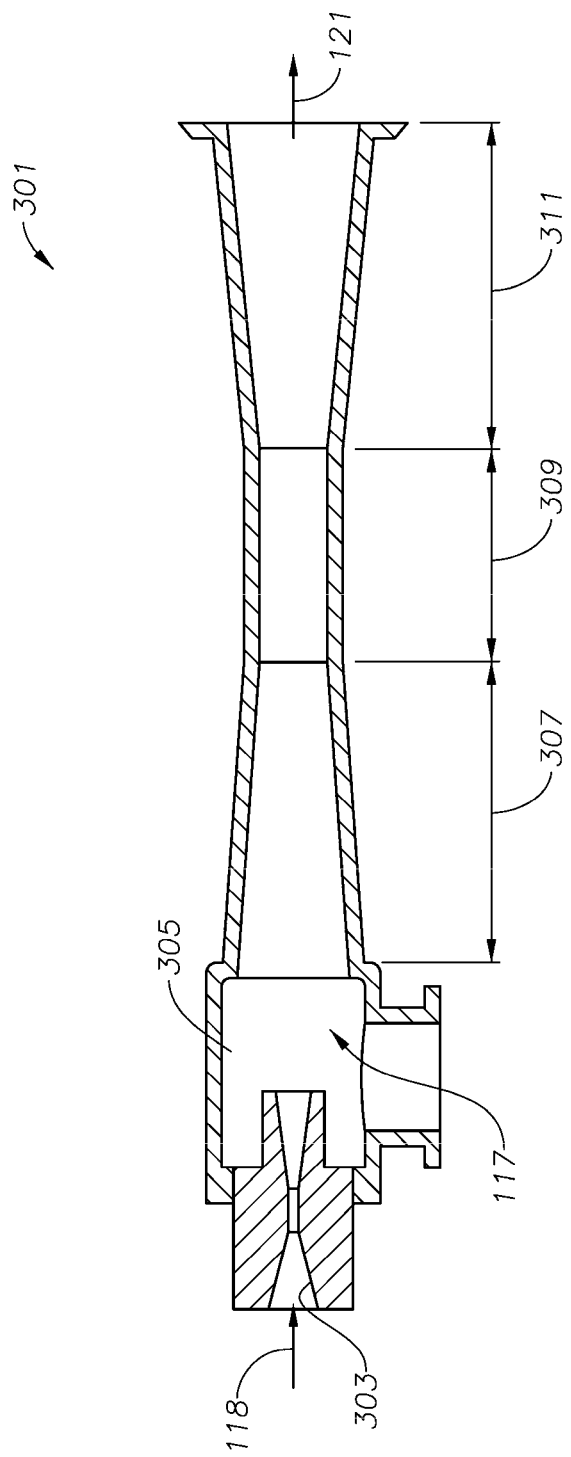
FIG. 3 is a schematic illustration of an eductor useful in the process and system in FIG. 1 above.

FIG. 3 illustrates an eductor 301 (with a full assembly body 119) useful in the process of the present invention for increasing the overall pressure of the first reactor hydrocarbon effluent. The eductor comprises a nozzle 303, a suction chamber 305, a converging diffuser 307, an elongated throat 309, and a diverging diffuser 311. During operation, a high pressure stream of a motive fluid 118 is injected into the suction chamber 305 at a high velocity. By operation of the Venturi principle, the jet of the motive fluid creates a negative pressure gradient inside the suction chamber. As a result, the process fluid (such as the first reactor hydrocarbon effluent) 117 is suctioned into the suction chamber 305 and admixed with the motive fluid. The high-velocity mixed fluid then travels through the converging diffuser 307, the throat 309, and exits the eductor at the end of the divergent diffuser 311 as an eductor effluent 121. Compression of the mixture to discharge pressure takes place as the velocity energy is converted into pressure as the mixture decelerates through the diffuser and divergent section. As a result, the overall pressure of the eductor effluent 121 can be increased substantially over the overall pressure of stream 117 before it enters the suction chamber 305. The eductor 301 has an elongated body 119 from the entrance of the nozzle 303 and the exit of the diverging diffuser 311.

Eductors can be designed for critical flow or sub-critical flow services. Eductors designed for pressure ratios greater than 2 will usually have critical flow (i.e., sonic velocity) through the diffuser throat. For lower pressure ratios, subcritical (i.e., subsonic) flow occurs through the diffuser throat. For best efficiency, critical-flow eductors work best at rated pressure ratios between 6 and 10. Pressure ratio, also known as compression ratio, is the ratio of the absolute pressure at the eductor discharge to the absolute pressure at the eductor suction.

One advantage of using eductors over compressors is that eductors can be utilized with high temperature process streams to compress with no moving parts, minimal vibration, no electricity usage, low noise level, lower equipment and installation cost, higher reliability in severe services, and minimum maintenance repair and operating attention. Eductors can be mounted on the outlet of the reactors to enable low reactor outlet pressures, including sub atmospheric pressure.

One skilled in the art can design the geometry, pressure distribution, velocity distribution, and other parameters of the eductor system depending on the entering pressure and temperature of the stream 117 and the desired pressure and temperature of the stream 121, based on teachings in, among others, Chemical Engineers' Handbook (Fifth Edition, Section 6-30). One skilled in the art can determine operation conditions of the eductor system such as:

(I) Capacity: The vapor-handling capability of an ejector system or ejector stage in mass flow units, typically in kilograms per hour of dry air equivalent (DAE) at the design suction pressure;

(II) Compression Ratio (or Pressure Ratio): The ratio of the absolute pressure at the ejector discharge, $P_2$, to the absolute pressure at the ejector suction, $P_1$;

(III) Critical (Critical Flow, Critical Stage): A condition in which sonic or supersonic velocities exist in the ejector, identified by gas expansion and compression ratios which exceed about 2:1;

(IV) Entrainment Ratios: The ratio of the mass flow rate of gas entrained to mass flow rate of air which would be entrained by the same ejector operating under the same conditions;

(V) Temperature Entrainment Ratio: The ratio of the mass flow rate of air or steam at 21° C. to the mass flow rate of air or steam at a higher temperature that would be entrained by the same ejector operating under the same conditions;

(VI) Expansion Ratio: The ratio of the motive fluid inlet pressure ($P_m$) to the entrained fluid inlet pressure ($P_1$);

(VII) Dry Equivalent Air (DAE): The flow in kg/hr of dry air at 21° C. which will produce the same suction pressure as the load mixture for which an ejector stage was designed. Heat Exchange Institute (HEI) standard correction factors for temperature and molecular weight are used to convert gas and vapor load mixtures to equivalent air loads;

(VIII) MDP (Maximum Discharge Pressure): In critical ejector stages only, the stage discharge pressure below which the ejector is always stable, operating on its basic performance curve. This limiting pressure varies with both the motive steam pressure and the load; and (IX) Ratio of steam flow to saturated water vapor flow: the motive steam requirement to compress one pound of water vapor, an intermediate value used to calculate the loading requirement.

One or multiple eductor may be used in the process and system of the present invention. Where multiple eductors are used, they are preferably operated in parallel under the same or different operation conditions.

By using an eductor between the outlet of the first reactor and the downstream washing vessel, one can effectively enable (i) a low sub-atmospheric overall pressure of the first reactor hydrocarbon effluent at the outlet of the first reactor; and (ii) the overall pressure of the fluid stream (the eductor effluent) entering into the washing vessel and subsequent separation vessels, such as the first separation sub-system for separating C5 hydrocarbons from light components, raised to atmospheric level, or even higher where desired. Unless a sufficient quantity of co-feedstock such as a C1-C4 hydrocarbon is also fed into the first reactor, it is typically desired that the overall pressure of the first rector effluent at the exit on the first reactor be sub-atmospheric, in order to achieve a high level of conversion of acyclic C5 hydrocarbons to CPD. The increased overall pressure of the eductor effluent, desirably above atmospheric level, minimizes ingress of oxygen/air into the system and the formation of undesirable species.

The eductor effluent comprises, in addition to the components in the first reactor hydrocarbon effluent, the motive fluid. It is highly desired that the motive fluid does not comprise a component that would undergo Diels-Alder reaction with CPD. It is also highly desired that in the eductor system, reactions between and among CPD and other diolefins, such as Diels-Alder reactions, that results in the formation of DCPD and hetero dimers, are minimized.

In the process of the present invention, the stream of the motive fluid when entering the suction chamber can have an overall pressure in the range from 100 to 10,000 kilopascal and/or a temperature in the range from 30 to 700° C., depending on the overall pressure and temperature of the first reactor hydrocarbon effluent at the outlet of the first reactor and the desired overall pressure and temperature of the eductor effluent at the exit thereof.

The motive fluid can be a material selected from C1-C4 hydrocarbons such as methane, fuel gas, natural gas from the grid; steam; C5 hydrocarbons such as n-pentane and isopentane; benzene and alkylated benzenes (including toluene and xylenes); alkylated naphthalenes (such as methylnaphthalenes), and combinations and mixtures thereof. The phase state of the motive fluids can be either vapor, liquid, or two-phase mix. Steam is the most common motive fluid used in process plants because of its relatively low cost, availability, recoverability by condensers, and compatibility with most fluids to be compressed. Quench oils, such as toluene and alkylnaphthalenes may be advantageously used from the perspectives of dew point control and heavy component solvation, especially if they are also used as at least a part of the wash oil described below. However, in the present invention, methane and pentanes may be advantageous in certain situations due to their presence in the first reactor hydrocarbon effluent. Methane can be especially preferred in certain examples because relatively pure methane gas recovered from the light components-rich separation sub-system described below, preferably desorbed at ambient temperature in a PSA or RCPSA process, can be recycled and used to simultaneously compress and quench the high-temperature first reactor hydrocarbon effluent to an intermediate pressure level suitable for heat recovery, separation, and further compression.

Desirably, the eductor used in the process of the present invention is operated under eductor conditions including at least one of: (i) compression ratio in the range from 1 to 20; (ii) an entrainment ratio in the range from 0.05 to 3, and (iii) an expansion ratio in the range from 5 to 100.

The eductor effluent in the process of the present invention can have (i) an overall pressure in the range from 100 kilopascal to 400 kilopascal and/or (ii) a temperature in the range from 30° C. to 700° C., depending on the overall pressure and temperature of the first reactor hydrocarbon effluent at the outlet from the first reactor. In general, the overall pressure of the eductor effluent is higher than that of the first reactor hydrocarbon effluent, and its temperature is lower than that of the first reactor hydrocarbon effluent at the outlet of the first reactor. Thus, the eductor can optionally function to quench down the first reactor hydrocarbon effluent, in addition to its main purpose of increasing the overall pressure. This can reduce side reactions that may occur in the first reactor hydrocarbon effluent at elevated temperatures.

While reference may be made to eductor in the singular, for commercial scale production facilities there will preferably be multiple eductors operating in parallel. The number will be dependent on total reactor effluent amount, selection of motive fluid, pressure of motive fluid, target discharge pressure and other engineering design considerations.

Cooling of the Eductor Effluent

To prevent undesirable side reactions, such as thermal cracking, condensation of PNAs, and premature Diels-Alder reactions of reactive diolefinic species, especially CPD, it is highly desired that the eductor effluent is cooled down once it exits the eductor. To that end, the eductor effluent may be passed through at least one heat exchanger located next to the exit from the eductor where its temperature is lowered to a range from Tc1° C. to Tc2° C., where Tc1 and Tc2 can be, independently, 20, 50, 80, 150, 200, 250, 300, 350, 400, or 450° C., as long as Tc1<Tc2. Alternately or additionally, the eductor effluent may be contacted with a quench liquid so that the temperature is lowered to a range from Tc1° C. to Tc2° C., where Tc1 and Tc2 can be, independently, 20, 40, 50, 60, 80, 100, 120, 140, 150, 160, 180, 200, 220, 240, 250, 260, 280, 300, 320, 340, 350, 360, 380, 400, 420, 440, or 450, as long as Tc1<Tc2.

Washing/Quenching of the Eductor Effluent

The eductor effluent comprises non-negligible amounts of heavy components produced in the first reactor, including but not limited to: polynuclear aromatic species (naphthalene and alkylated naphthalenes, anthracene and alkylated anthracenes, phenanthrene and alkylated phenanthrenes), DCPD, products formed as a result of undesired Diels-Alder reactions between CPD and acyclic diolefins. It is highly desired that these heavy components, especially C8+ hydrocarbons, are at least partly removed from the eductor effluent such that contamination of the C5-rich fraction and subsequent contamination of DCPD fractions by them is avoided. For example, naphthalene is very difficult to be removed from DCPD by distillation; also naphthalene and heavier PNAs can condense to form solids which can foul equipment. Therefore, naphthalene and heavier PNAs are desirably removed from the eductor effluent before it is further processed.

Advantageously, such heavy components can be effectively removed in a vessel by contacting the stream of the eductor effluent, preferably after it is being partially cooled down, with a wash oil. To that end, the wash oil, desirably in liquid phase during operation, can be sprayed into the washing vessel as liquid droplets when contacting the substantially vapor stream of the eductor effluent. Additionally or alternatively, the substantially vapor stream of the eductor effluent can be sent to a suitable gas-liquid contacting washing vessel capable of handling fouling services (e.g., a tower with grids and/or random packing). Sufficient contact between the eductor effluent and the liquid wash oil results in the extraction of the heavy components (i.e., C8+ hydrocarbons) from the substantially vapor stream of the eductor effluent into the wash oil liquid. A small amount of the wash oil may be entrained in the washed eductor effluent vapor stream at a low vapor pressure. The entrained wash oil can be removed subsequently where necessary.

In the washing vessel, the eductor effluent vapor stream can be quenched down further to a temperature in a range from 10 to 300° C., preferably from 20 to 100° C. Thus, from the washing vessel, a vapor stream of the eductor effluent, washed and cooled, is obtained. In addition, a wash oil liquid stream, comprising multiple-ring aromatics mentioned above, may also be obtained.

Various wash oils can be used. Non-limiting examples of the wash oil include: cyclohexane; monoalkyl, dialkyl, and trialkyl cyclohexanes; benzene; monoalkyl, dialkyl, and trialkyl benzenes; monoalkyl, dialkyl, trialkyl, and tetraalkyl naphthalenes; other alkylated multiple-ring aromatics; and mixtures and combinations thereof. Preferred wash oils are: alkyl benzenes and mixtures thereof (herein referred to as light wash oil); and alkyl naphthalenes and mixtures thereof (herein referred to as heavy wash oil). More preferably, toluene, especially relatively pure toluene with a purity of at least 50 wt %, or alkylnaphthalene(s), especially those with purity of at least 50 wt %, is used as the wash oil.

The wash oil and the motive fluid may or may not have common or identical component(s). Depending on the normal boiling point of the motive fluid and its interaction with the wash oil and other components in the first reactor hydrocarbon effluent, the motive fluid may be distributed in the washed eductor effluent vapor stream, the wash oil liquid stream, or both.

In the fluid channel from the first reactor to the washing vessel, including the eductor and the heat exchanger in between, if any, and inside the washing vessel, dimerization between CPD molecules may occur to form DCPD, and CPD may react with acyclic diolefins to form other C10+ hydrocarbons. A major portion of these heavy components, if formed, are partitioned in the wash oil liquid stream exiting the washing vessel. If the wash oil liquid stream is sent to a fuel disposition or other low value disposition directly, a portion of the CPD produced in the first reactor would be downgraded to low value. To reduce such undesirable yield loss, one can treat the wash oil liquid stream, together with other, down-stream produced streams also comprising such heavy components and/or wash oil, in a vessel operated under conditions favoring reverse dimerization, to obtain an upper C5-rich stream and a lower wash oil-rich stream containing residual C8+ and the wash oil. The upper C5-rich stream may be fed directly or indirectly to a second reactor as part of the first C5-rich fraction. The lower wash oil-rich stream can be further distilled to recover at least a portion of the wash oil, which can be recycled to the wash vessel directly or indirectly. Such conditions favoring reverse dimerization include, e.g., a temperature in the range from 150 to 350° C., preferably, from 170 to 260° C., a pressure in a range from 21 to 345 kilopascal absolute, preferably from 21 to 138 kilopascal absolute, and a residence time from 0.01 to 10 hours, preferably from 0.1 to 4 hours. If the motive fluid is identical with the wash oil, part of the recovered wash oil may be recycled to the eductor as the motive fluid as well. Advantageously, at least a portion of the wash oil liquid stream effluent from the wash oil tower is used directly as the motive fluid.

Separation of the Eductor Effluent

The eductor effluent, which is preferably cooled by a heat exchanger as described above, and washed in a washing vessel as described above is then supplied via a fluid communication channel to a first separation sub-system and processed in the first separation sub-system to obtain (i) a C5-rich fraction that is depleted of C1-C4 hydrocarbons and hydrogen, and desirably, depleted of heavy components such as C8+ hydrocarbons, and (ii) a light components stream that is desirably depleted of C5+ hydrocarbons. Due to the nature of the reactions taking place in the first reactor, substantial volume of hydrogen is present in the eductor effluent. Effective separation of hydrogen and C1-C4 light hydrocarbons from the C5 hydrocarbons (including CPD) needs to take into consideration that much of the C5 hydrocarbons can be held as vapor in the hydrogen/light hydrocarbon stream.

It is highly desirable that the light components-rich fraction obtained from the first separation sub-system comprises C5 hydrocarbons at a very low concentration. To that end, compression of the mixture of C5 and light components followed by cooling and separation can be used. Desirably, a compression train with inter-stage cooling and liquid/vapor separation can be advantageously used as the first separation sub-system to minimize the loss of C5 hydrocarbons to the hydrogen and light hydrocarbon stream. Depending on the nature of the motive fluid, it may be distributed in the first C5-rich stream, the light components stream, or both. Desirably, the motive fluid is chosen such that its concentration in the first C5-rich stream is either significantly higher or significantly lower than in the light components fraction.

Exemplary compression trains with inter-stage cooling and liquid/vapor separation are those comprising at least 3-stages of compression/inter-stage cooling with an exiting pressure from the last stage of at least 100 psia (689 kilopascal absolute).

From the first separation sub-system (a compression train, e.g.), one or more streams of C5-rich hydrocarbon (the first C5-rich fraction) may be obtained from the multiple stages. Where multiple streams of the first C5-rich fractions are obtained, two or more of them may be optionally combined into a single first C5-rich rich fraction stream and then processed together subsequently. The first C5-rich fraction generally comprises: (i) CPD; (ii) unreacted C5 hydrocarbon(s) from the C5 feedstock such as n-pentane; and (iii) cyclopentane to and cyclopentene.

The first C5-rich fraction may further comprise a portion of the wash oil and/or the motive fluid, especially if the wash oil or motive fluid contains C6 and C7 hydrocarbons, such as cyclohexane and alkylcyclohexanes, benzene and alkylbenzenes (e.g., toluene). Such C6+ components may be removed subsequently where necessary. Even if high boiling point wash oils such as alkyl naphthalenes are used, the first C5-rich fraction may comprise one-ring aromatics (as by-products from the first reactor) such as benzene at a low concentration.

From the first separation sub-system (the first liquid/vapor separator in a multi-stage compression train, e.g.), an optional heavy-containing stream may be produced, especially at one of the early stages, comprising wash oil, heavy C6+ motive fluid (if used), and C8+ hydrocarbons (DCPD, and other products as a result of the Diels-Alder reactions between CPD and other dienes, e.g.), and the like. Such heavy stream can be in non-negligible quantity if high boiling point wash oil such as methylnaphthalene(s) is used. If such heavy stream is produced from the compression train, it may be advantageously combined with the wash oil liquid stream produced from the washing vessel described above, and then processed together subsequently.

From the first separation sub-system (a compression train, e.g.), a light components-rich fraction comprising hydrogen and C1-C4 hydrocarbons (produced in the first reactor or introduced partly as the motive fluid (if a C1-C4 motive fluid is used)) is also obtained. This light components-rich fraction is desirably depleted of C5 components, especially CPD, or at least minimized, such that C5 molecules are used to the highest degree in the process of the present invention.

Separation of the Light Components-Rich Fraction and Recycling of Hydrogen and/or Light Hydrocarbons A significant component of the light components-rich fraction coming from the first separation sub-system separating the eductor effluent is hydrogen gas. C1-C4 hydrocarbons are produced at small quantities in the first reactor from the C5 feedstock. Alternatively, in certain exemplary processes of the present invention, a C1-C4 light hydrocarbon, such as $CH_4$, may be supplied to the first reactor as a co-feedstock or to the eductor as the motive fluid, resulting in higher concentrations of the C1-C4 light hydrocarbons in the light components-rich fraction obtained from the first separation sub-system.

Given the large quantity of hydrogen produced in the process, it is desirable to separate the light components-rich fraction to obtain a higher purity hydrogen stream, which can be used or sold as a highly valuable industrial gas. To that end, various processes and equipment may be used to recover and concentrate hydrogen, such as pressure-swing adsorption (PSA), rapid cycle pressure-swing adsorption (RCPSA), thermal-swing adsorption (TSA), cryogenic processes, membrane separation, and the like, with PSA or RCPSA being preferred. By using any of these processes or any combinations thereof, it is possible to obtain three gas streams from the light components-rich fraction: a hydrogen-rich stream comprising hydrogen at a purity of at least 95 mol %, based on the total moles of the hydrogen-rich stream; a middle stream comprising hydrogen and C1-C4 hydrocarbons that is preferably low in C2+ hydrocarbons if the stream is methane-rich or C3+ hydrocarbons if the stream is ethane-rich; and a C1-C4-rich hydrocarbon stream which may also contain C5+ hydrocarbons which can be subsequently recovered by washing or low temperature fractionation (absorber, e.g.). A portion of the hydrogen-rich stream and/or a portion of the middle stream (if C1-C4 hydrocarbon is co-fed into the first reactor) can be recycled to the first reactor. Additionally or alternatively, at least a portion of the middle stream and/or the C1-C4 hydrocarbon stream can be used as fuel gas to produce the thermal energy needed for certain steps (such as the conversion process in the first reactor) in the process of the present invention. Alternatively, the C1-C4-rich hydrocarbon stream can be utilized as the motive fluid, a feedstock for other process such as light olefins production and/or further processed to obtain an LPG fraction.

As discussed above, the recycle hydrogen may be advantageously admixed with at least a portion of the C5 feedstock before being fed into the first reactor to reduce coke formation on the catalyst particles, thereby increasing the life of the catalyst used in the first reactor. Additionally or alternatively, the recycle hydrogen may be fed separately into the first reactor. Additionally or alternatively, the recycle hydrogen may be utilized for rejuvenation or reduction of the catalyst.

Dimerization of the First C5-Rich Fraction

The first C5-rich fraction advantageously comprises CPD at a high concentration in a range from ca1 wt % to ca2 wt %, based on the total weight of C5 hydrocarbons in the first C5-rich fraction, where ca1 and ca2 can be, independently, 20, 25, 30, 35, 40, 45, 50, 55, 60, 65, 70, 75, 80, 85, or 90, as long as ca1<ca2. Such CPD may be used directly as a CPD feed for the production of, e.g., norbornene, vinyl norbornene, ethylidene norbornene, hydrocarbon resin adhesives or tackifiers, unsaturated polyester resins, cyclopentane, and/or cyclopentene.

Additionally or alternatively, at least a portion of the first C5-rich fraction can be supplied to a first dimerization reactor (the second reactor in the system) operating under a first set of dimerization conditions, where a portion of the CPD is advantageously converted into DCPD. This can be highly desirable because DCPD is much more stable than CPD, and therefore can be stored and/or transported to a different location where it is used as DCPD or converted into CPD and used for the production of value-added products.

The first dimerization reactor (the second reactor in the system) can be advantageously a plug flow reactor, a back mixed reactor, a continuous stirred-tank reactor, a boiling point reactor, and/or a baffled reactor; additionally the reactor may contain heat transfer devices such as coils. The first dimerization reactor may consist of one or more reaction zones within a single vessel or in multiple vessels and may include one or more heat exchanging devices within the reaction zones or between the reaction zones.

The first set of dimerization conditions in the first dimerization reactor can advantageously include: a temperature in the range from Tb1° C. to Tb2° C., where Tb1 and Tb2 can be, independently, 30, 50, 60, 80, 100, 120, 140, 150, 160, 180, 200, 220, 240, or 250, as long as Tb1<Tb2; an absolute pressure in the range from Pb1 kilopascal to Pb2 kilopascal, where Pb1 and Pb2 can be, independently, 345, 350, 400, 450, 500, 550, 600, 700, 800, 900, 1000, 1500, 2000, 2500, 3000, 3500, 4000, 4500, 5000, 6000, 6500, 6894, or 7000, as long as Pb1<Pb2; and a residence time in the range from Tr1 minutes to Tr2 minutes, where Tr1 and Tr2 can be, independently, 1, 10, 20, 30, 40, 50, 60, 70, 80, 90, 100, 110, 120, 130, 140, 150, 160, 170, 180, 190, 200, 210, or 220, as long as Tr1<Tr2. Preferably, if two dimerization reactors in series are utilized in the system, the first set of dimerization conditions include a temperature in the range from 70 to 130° C., a total pressure in the range from 689 to 3447 kilopascal absolute, and a residence time in the range from 20 to 200 minutes, such as from 100 to 200 minutes; preferably, if three dimerization reactors in series are utilized in the system, the first set of dimerization conditions include a temperature in the range from 90 to 140° C., a total pressure in the range from 689 to 3447 kilopascal absolute, and a residence time in the range from 1 to 30 minutes.

A portion of the CPD contained in the first C5-rich fraction supplied into the first dimerization reactor is converted into DCPD. At the outlet of the second reactor (the first dimerization reactor), a second reactor effluent is obtained comprising CPD and DCPD. Preferably, the degree of conversion in the second reactor is limited so that high purity DCPD in may be produced; i.e., the extent of conversion is limited so that the quantity of CPD co-dimers with acyclic dienes and mono olefins is maintained below a level so as to be able to obtain the desired purity of DCPD.

Separation of the First DCPD-Rich Fraction

At least a portion of the second reactor effluent is then supplied to a second separation device, such as a distillation column, where a first DCPD-rich fraction (as a lower stream such as a bottom effluent from the column, e.g.) and a second C5-rich fraction (as an upper stream such as an overhead effluent from the column, e.g.) are obtained. Advantageously, the first DCPD-rich fraction can have a DCPD concentration of C(DCPD)1 wt %; and $x1 \leq C(DCPD)1 \leq x2$, wherein x1 and x2 can be, independently, 80, 82, 84, 85, 86, 88, 90, 91, 92, 93, 94, 95, 96, 97, 98, 99, 99.2, 99.4, 99.5, 99.6, 99.8, or 100, as long as x1<x2. Ultra high purity DCPD (i.e., UHP DCPD) with a concentration of at least 98 wt %, 99 wt %, or even 99.5 wt %, can be obtained as the first DCPD-rich fraction. At least a portion of the first DCPD-rich fraction can be optionally supplied to at least another separation device, such as a distillation column, where the purity of the first DCPD-rich fraction can be further increased. CPD concentration in the second C5-rich fraction tends to be lower than in the first C5-rich fraction.

Dimerization of the Second C5-Rich Fraction

At least a portion of the second C5-rich fraction obtained from the second separation device may advantageously comprise CPD at a high concentration in the range from ca3 wt % to ca4 wt %, based on the total weight of C5 hydrocarbons in the second C5-rich fraction, where ca3 and ca4 can be, independently, 1, 5, 10, 20, 25, 30, 35, 40, 45, 50, 55, or 60, as long as ca3<ca4. Such CPD in the second C5-rich fraction may be directly used as a CPD feed for the production of, e.g., norbornene, vinyl norbornene, ethylidene norbornene, hydrocarbon resin adhesives or tackifiers, unsaturated polyester resins, cyclopentane, and/or cyclopentene.

Additionally or alternatively, the second C5-rich fraction can be supplied to a second dimerization reactor (the third reactor in the system) operating under a second set of dimerization conditions, where a portion of the CPD is advantageously converted into DCPD, similar to the operation in the first dimerization reactor (the second reactor in the system), but preferably operating at a higher temperature and/or longer residence time to enable satisfactory conversion of the lower concentration CPD.

Thus, the second set of dimerization conditions in the second dimerization reactor can advantageously include: a temperature in the range from Tb3° C. to Tb4° C., where Tb3 and Tb4 can be, independently, 30, 50, 60, 80, 100, 120, 140, 150, 160, 180, 200, 220, or 240, or 250, as long as Tb3<Tb4; an absolute pressure in the range from Pb3 kilopascal to Pb4 kilopascal, where Pb3 and Pb4 can be, independently, 345, 350, 400, 450, 500, 550, 600, 700, 800, 900, 1000, 1500, 2000, 2500, 3000, 3500, 4000, 4500, 5000, 6000, 6500, 6894, or 7000, as long as Pb3<Pb4; and a residence time in the range from Tr3 minutes to Tr4 minutes, where Tr3 and Tr4 can be, independently, 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 as long as Tr3<Tr4. Preferably, if two dimerization reactors in series are utilized in the system, the second set of dimerization conditions include a temperature in the range from 75 to 140° C., such as from 100 to 140° C., a total pressure in the range from 689 to 3447 kilopascal absolute, and a residence time in the range from 100 to 300 minutes, such as from 150 to 300 minutes; preferably, if three dimerization reactors in series are utilized in the system, the second set of dimerization conditions include a temperature in the range from 100 to 140° C., a total pressure in the range from 689 to 3447 kilopascal absolute, and a residence time in the range from 1 to 30 minutes.

The second dimerization reactor (the third reactor in the system) can be a reactor similar to the first dimerization reactor (the second reactor in the system).

A portion of the CPD contained in the second C5-rich fraction supplied into the second dimerization reactor is converted into DCPD. At the outlet of the second dimerization reactor, a third reactor effluent is obtained comprising CPD and DCPD. Preferably, the degree of conversion in the third reactor is limited so that high purity DCPD may be produced; i.e., the extent of conversion is limited so that the quantity of CPD co-dimers with acyclic dienes and mono olefins is maintained below a level so as to be able to obtain the desired purity of DCPD.

Separation of a Second DCPD-Rich Fraction

At least a portion of the third reactor effluent can then be supplied to a third separation device, such as a distillation column, where a second DCPD-rich fraction (as a lower stream such as a bottom effluent from the column, e.g.) and a third C5-rich fraction (as an upper stream such as an overhead effluent from the column, e.g.) are obtained. Advantageously, the second DCPD-rich fraction can have a DCPD concentration of C(DCPD)2 wt %; and x3≤C(DCPD) 2≤x4, wherein x3 and x4 can be, independently, 40, 50, 60, 65, 70, 75, 80, 82, 84, 85, 86, 88, 90, 91, 92, 93, 94, 95, 96, 97, 98, or 99 as long as x3<x4. Usually, the purity of the second DCPD-rich fraction is lower than the first DCPD-rich fraction because of the lower ratio of CPD to acyclic diolefins in the second C5-rich fraction than the first C5-rich fraction. Nonetheless, very high purity DCPD (HP DCPD) with a concentration of at least 90 wt %, or 92 wt %, or 93 wt %, or even 95 wt % can be obtained as the second DCPD-rich fraction. At least a portion of the second DCPD-rich fraction can be optionally supplied to at least another separation device, such as a distillation column, where the purity of the second DCPD-rich fraction can be further increased. Likewise, CPD concentration in the third C5-rich fraction tends to be lower than in the second C5-rich fraction.

Dimerization of the Third C5-Rich Fraction

At least a portion of the third C5-rich fraction obtained from the third separation device may advantageously comprise CPD at a concentration in the range from ca5 wt % to ca6 wt %, based on the total weight of the C5 hydrocarbons in the third C5-rich fraction, where ca5 and ca6 can be, independently, 1, 5, 10, 15, 20, 25, 30, 35, 40, 45, 50, 55, or 60, as long as ca5<ca6. Such CPD in the third C5-rich fraction may be directly used as a CPD feed for the production of, e.g., norbornene, vinyl norbornene, ethylidene norbornene, hydrocarbon resin adhesives or tackifiers, unsaturated polyester resins, cyclopentane, and/or cyclopentene.

Additionally or alternatively, at least a portion of the third C5-rich fraction can be supplied to a third dimerization reactor (the fourth reactor in the system) operating under a third set of dimerization conditions, where a portion of the CPD is advantageously converted into DCPD, similar to the operation in the first dimerization reactor (the second reactor in the system).

The third dimerization reactor (the fourth reactor in the system) can be a reactor similar to the first dimerization reactor (the second reactor in the system), but preferably operating at a higher temperature and/or longer residence time to enable satisfactory conversion of the lower concentration CPD.

Desirably, a majority of the CPD contained in the third C5-rich fraction supplied into the third dimerization reactor is converted into DCPD. Additionally or alternatively, it is desirable to react acyclic C5 diolefins (e.g., 1,3-pentadiene; 1,4-pentadiene, 1,2-pentadiene, and/or 2-methyl-1,3-butadiene) with CPD to produce co-dimers in the third dimerization reactor. Additionally or alternatively, additional streams containing acyclic C5 diolefins (e.g., steam cracked naphtha, light cat naphtha, heavy cat naphtha) and/or C6 diolefins (e.g., methyl cyclopentadienes and hexadienes) may be added to the feed to the third dimerization reactor. Additionally, trimers and tetramers of the C5 and C6 species may also be advantageously produced. At the outlet of the third dimerization reactor, a fourth reactor effluent is obtained comprising CPD and DCPD, preferably in combination with other C5 co-dimers, -trimers, and/or -tetramers.

Thus, the third set of dimerization conditions in the third dimerization reactor can advantageously include: a temperature in the range from Tb5° C. to Tb6° C., where Tb5 and Tb6 can be, independently, 30, 50, 60, 80, 100, 120, 140, 150, 160, 180, 200, 220, 240, or 250, as long as Tb5<Tb6; an absolute pressure in the range from Pb5 kilopascal to Pb6 kilopascal, where Pb5 and Pb6 can be, independently, 345, 350, 400, 450, 500, 550, 600, 700, 800, 900, 1000, 1500, 2000, 2500, 3000, 3500, 4000, 4500, 5000, 6000, 6500, 6894, or 7000, as long as Pb5<Pb6; and a residence time in the range from Tr5 minutes to Tr6 minutes, where Tr5 and Tr6 can be, independently, 100, 200, 300, 400, 500, 600, 700, 800, 900, or 1000, as long as Tr5<Tr6. Preferably, the third set of dimerization conditions include a temperature in the range from 80 to 150° C., such as from 100 to 150° C., a total pressure in the range from 689 to 3447 kilopascal absolute, and a residence time in the range from 150 to 300 minutes.

Separation of a Third DCPD-Rich Fraction

At least a portion of the fourth reactor effluent can then be supplied to a fourth separation device, such as a distillation column, where a third DCPD-rich fraction (as a bottom effluent from the column, e.g.) and fourth C5-rich fraction (as an overhead effluent from the column, e.g.) are obtained. Advantageously, the third DCPD-rich fraction can have a DCPD concentration of C(DCPD)3 wt %; and x5≤C(DCPD) 3≤x6, wherein x5 and x6 can be, independently, 20, 30, 40, 45, 50, 55, 60, 65, 70, 75, 80, 82, 84, 85, 86, 88, 90, 91, 92, 93, 94, or 95, as long as x5<x6. Usually, the purity of the third DCPD-rich fraction is lower than the second DCPD-rich fraction because of the lower ratio of CPD to acyclic dienes in the third C5-rich fraction than the second C5-rich fraction. Nonetheless, moderate purity DCPD with a concentration of at least 70 wt %, 75 wt %, 80 wt %, 85 wt %, or 90 wt % can be obtained as the third DCPD-rich fraction. At least a portion of the third DCPD-rich fraction can be optionally supplied to at least another separation device, such as a distillation column, where the purity of the third DCPD-rich fraction can be further increased. Likewise, CPD concentration in the fourth C5-rich fraction tends to be lower than in the third C5-rich fraction.

Recycling of C5-Rich Fractions to the First Reactor

At least a portion of the first, second, third, and fourth C5-rich fractions described above, if produced at all in the process of the present invention, can be recycled to the first reactor described above, e.g., via a fluid communication channel, where the unreacted C5 hydrocarbon(s) and partially converted C5 hydrocarbons from the C5 feedstock can be further converted into CPD.

The first, second, third, and fourth C5-rich fractions, if produced, may contain C6+ hydrocarbons, such as cyclohexane, benzene, toluene, and the like. To prevent the accumulation of such C6+ components in the reaction product in the first reactor, it is highly desirable that, prior to being recycled to the first reactor, at least a portion of the C6+ components is separated and removed from the C5-rich stream in another separation device, such as a distillation column, to produce a fifth C5-rich stream and a C6+-rich stream. Thus, a purified fifth C5-rich fraction is then recycled to the first reactor, e.g., via a fluid communication channel.

Forming Mogas Blending Components from the C5+ Components

Mogas is a blended mixture comprising C4 through C12 hydrocarbons having an initial normal boiling point of about 35° C. and a final boiling point of about 200° C. Mogas is used primarily as fuel for internal combustion engines in automotive vehicles. There are many different mogas specifications that have been mandated by various local, state, or national governmental agencies. One example is Reid Vapor Pressure (RVP) of final mogas product. The vapor pressure of mogas is a measure of its volatility and high vapor pressures resulting in high evaporative emissions of smog-forming hydrocarbons.

From a performance standpoint, an important attribute of mogas is its octane rating. Linear paraffinic hydrocarbons (i.e., straight-chain saturated molecules) tend to have lower octane ratings than other hydrocarbons, such as aromatics, olefins, and branched paraffins. To that end, many of the refining processes used in petroleum refineries are designed to produce hydrocarbons with these latter molecular configurations. For example, catalytic reforming is a widely practiced industrial process used to convert naphtha feed typically having low-octane ratings into high-octane liquid products to make premium blending stocks for mogas. The process converts paraffins and naphthenes into high-octane aromatic hydrocarbons. However, naphtha catalytic reforming is limited to C6+ feedstocks.

Converting n-pentane to isopentane (a/k/a i-pentane) can result in a favorable increase in octane, but also an unfavorable increase in the RVP. Conversion of n-pentane to cyclopentyl and internal olefinic species—which occurs in the first reactor in the present invention—favorably increases the octane and favorably decreases the RVP. DCPD-rich streams may also be partially or fully hydrogenated to produce a low RVP/higher octane blend component.

Thus, additionally or alternatively, at least a portion of the first, second, third, fourth, and fifth C5-rich fractions and the C6+-rich stream described above, if produced at all in the process of the present invention, can be optionally combined with additional streams containing diolefins (e.g., steam cracked naphtha, light cat naphtha, heavy cat naphtha) and can be selectively hydrogenated to produce a mogas component. Because the first, second, third, fourth, and fifth C5-rich fractions contain high concentrations of unsaturated C5 hydrocarbons, including CPD and cyclopentene, once partially hydrogenated they tend to have higher octane-value and lower Reid Vapor Pressure (RVP) than the acyclic saturated C5 feedstock supplied to the first reactor. As used herein, a "selective hydrogenation" process is a treatment of a mixture comprising both diolefins and mono olefins with hydrogen in the presence of a selective hydrogenation catalyst under selective hydrogenation conditions favoring the conversion of diolefins into mono olefins over the conversion of mono olefins into saturates. Such selective hydrogenation may be carried out in a hydrogenation reactor having a hydrogenation catalyst loaded therein. It is highly desired that the selectively hydrogenated mogas component comprises diolefins at a total concentration not higher than 1.0 wt %, based on the total weight of the mogas component. Thus, mogas component can then be blended with additional mogas components to obtain mogas with the desired composition and properties.

Additionally or alternatively, prior to or after hydrogenation thereof, at least a portion of the first, second, third, fourth, and fifth C5-rich fractions described above, if produced at all in the process of the present invention, and/or a portion of their hydrogenated products, may be separated to obtain high-purity cyclopentene, cyclopentane, 2-methyl-1,3-butadiene, and/or 1,3-pentadiene, each of which can be used or sold as valuable industrial materials.

Non-limiting examples of hydrogenation catalyst include: palladium-based or nickel-based catalysts. Exemplary hydrogenation conditions include: a temperature in the range from 30-250° C. and a pressure in the range from 1,700-5,500 kilopascal absolute.

The present invention can be used to convert low value C5 feedstock into higher value CPD, DCPD, mogas components with high octane and/or lower RVP, cyclopentene, cyclopentane, 1,3-pentadiene, and the like, and hydrogen.

DESCRIPTION ACCORDING TO THE DRAWINGS

The drawings schematically illustrate the block flow diagrams of exemplary system(s) and sub-system(s) thereof of the present invention operating to implement exemplary process(es) or aspects thereof of the present invention. It should be understood that only major components are shown in the drawings. Auxiliary equipment such as control valves, pumps, heat exchangers, reboilers, recycle loop, and the like, although not all shown in all drawings, are used liberally throughout the whole process to manipulate stream and equipment thermodynamic conditions.

In the system 101 shown in FIG. 1, a C5 feedstock stream 103 comprising n-pentane at, e.g., at least 50 wt % is combined with a hydrogen co-feedstock stream 105 to form a combined stream 107, which is then combined with a recycle third C5-rich stream 109 to form a combined feed stream 111, which is fed to a first reactor 113 (also labeled R1). The molar ratio of hydrogen to the C5 feedstock in stream 111 can range from 0.1 to 3.0, preferably from 0.3 to 2.0, more preferably from 0.5 to 1.5. A major purpose of co-feeding hydrogen is to prevent coke formation on the catalyst, especially at locations where the in-situ produced hydrogen is at a relatively low concentration. The reactor 113 may be a fixed bed reactor with a bed of catalyst 115 loaded therein. The catalyst 115 is chosen from the compositions described above. Reactions of the acyclic C5 hydrocarbons in the presence of the catalyst particles are highly endothermic. Thus, reactor 113 is heated by external heating to maintain an internal temperature in the range from 450° C. to 800° C. The weight hourly space velocity is in the range from 1 to 100 hour$^{-1}$. A substantial portion of the C5 hydrocarbons in the feed 111 is converted into CPD and byproducts such as acyclic diolefins, acyclic mono olefins, cyclopentane, cyclopentene; light components including hydrogen and C1-C4 hydrocarbons; one-ring aromatics; and multiple-ring aromatics at a total conversion of n-pentane in the range from 50% to 99%. At the outlet of the first reactor 113, a first reactor hydrocarbon effluent 117 is drawn at a temperature in the range from 500 to 800° C. and at a total absolute pressure in the range from 20 to 100 kilopascal absolute.

The first reactor hydrocarbon effluent 117 can comprise CPD at a total concentration in the range from 15 wt % to 80 wt %, on the basis of the total weight of C5 hydrocarbons in the first reactor hydrocarbon effluent 117. Once it exits the first reactor 113, the first reactor hydrocarbon effluent stream 117 is suctioned into the suction chamber of an eductor 401 by a pressure gradient caused by the movement of a stream of high-velocity motive fluid 403 injected into the suction chamber. While only one eductor is shown in FIG. 1, it is possible, and preferable under certain circumstances to use multiple eductors operating in parallel to each other. The motive fluid can be, e.g., methane, toluene, or other materials described above. At the exit of the eductor 401, an eductor effluent 405, which is a mixture to of the first reactor hydrocarbon effluent and the motive fluid, is obtained at an overall pressure in the range from 100 to 400 kilopascal absolute, preferably from 100 to 200 kilopascal, and a temperature in the range from 30 to 700° C., preferably from 200 to 550° C. The eductor effluent 405 may be cooled down by one or more heat exchanger 119 to obtain a cooled eductor effluent 121 to avoid undesired side reactions such as thermal cracking, condensation of PNAs, and premature Diels-Alder reactions of reactive diolefinic species, especially CPD in downstream processes and equipment. A quantity of wash oil (not shown) may be added prior to and/or within exchanger to help prevent fouling.

The cooled eductor effluent 121 and a wash oil steam 125 are then fed into a washing vessel 123, where the eductor effluent is also quenched down to obtain a washed eductor effluent stream 129. The wash oil used in the example shown in FIGS. 1 and 2 comprises alkylnaphthalene(s) and/or alkylbenzene at a total concentration of at least 50 wt %, though other wash oil as described above may be used. Stream 129 comprises C5 components and light components from the eductor effluent. Stream 129 may also contain C6, C7, C8, and the wash oil at non-negligible amounts. A wash oil bottom stream 127, comprising the wash oil, one-ring aromatics and multiple-ring aromatics, is also obtained from the washing vessel 123.

The upper stream 129, as clean eductor effluent, is then supplied to a first separation sub-system 131 (also labeled SD1), e.g., via a fluid communication channel, where a first C5-rich stream 133, one or more additional C5-rich streams 134 (one shown in FIG. 1), and a light component stream 161 comprising hydrogen and C1-C4 hydrocarbons are obtained. The C5-rich streams 133 and 134 are advantageously depleted of C1-C4 hydrocarbons. Stream 133 can comprise one or more of C6, C7, C8+, partly from the motive fluid (if a C6+ motive fluid is used) and the heavy wash oil, at non-negligible amounts. Stream 134 desirably comprises C6, C7, C8+, and the heavy wash oil at significantly lower concentrations than stream 133. Preferably, stream 134 is essentially free of C10+ and the heavy wash oil. Stream 161 is fairly large in total volume, given the amount of hydrogen produced in the first reactor 113. To recover the non-negligible amount of C5 components present in stream 161, stream 161 is further contacted with a wash oil stream 165 in vessel 163 (sometimes also called "debutanizer" or "debutanizer section") to obtain a stream 167 comprising $H_2$ and C1-C4 hydrocarbons and depleted of C5 components. Wash oil stream 125 exiting debutanizer vessel 163 is then recycled to the washing vessel 123 as described above. Stream 167 can be further separated by using various equipment and processes (now shown), such as PSA, RCPSA, TSA, cryogenic method, and membrane separation, to obtain one or more of the following: (i) a high-purity $H_2$ stream; (ii) a $H_2$/C1-C4 hydrocarbon mixture stream; and (iii) a C1-C4-rich hydrocarbon stream.

Stream 133, to the extent it may comprise one or more of C6, toluene, C8+, and the heavy wash oil at non-negligible concentration(s), is fed into a heavy wash oil-removal column 135 together with stream 127 described above, where an upper stream 137 rich in C5 and depleted of C10+, and a lower stream 138 comprising C7 and C8+ are obtained. Stream 138 may be purified in a subsequent distillation column (not shown) to obtain an alkylnapthalene-rich stream, which can be recycled to vessel 163 and/or washing vessel 123 described above. Efforts should be taken to reduce reactions between CPD and acyclic diolefins in heat exchanger 191, vessels 123, 135, and the front end of the first separation sub-system 131. Nonetheless, because such side reactions may take place at various degrees, it is highly desirable that column 135 is operated under a condition such that reverse dimerization reaction is favored over dimerization, such that heavy components such as DCPD, reaction products between DCPD and acyclic diolefins are converted into CPD and other C5 components, and, therefore, CPD and other C5 components that otherwise would be lost to side reactions are at least partially recovered. To that end, the conditions in the column 135 comprise advantageously a column bottom temperature in the range from 150 to 350° C., preferably from 170 to 260° C., and a total absolute pressure in the range from 3 psia to 50 psia (21 to 345 kilopascal absolute), preferably from 20 psia to 40 psia (138 to 276 kilopascal absolute), and a residence time in the range from 0.01 to 10 hours, preferably from 0.1 to 4 hours.

Stream 137 and stream 134, both C5-rich and depleted of C10+, together as the first C5-rich fraction obtained from the first separation sub-system, is then delivered to the second reactor (also labeled R2, and called first dimerization reactor) 139 operating under a first set of dimerization conditions to convert a portion of the CPD contained therein into DCPD. The first set of dimerization conditions advantageously comprise: a temperature in the range from 30 to 250° C., preferably from 70 to 140° C., such as from 90 to 130° C., and a total absolute pressure in the range from 50 psia to 1000 psia (345 to 6895 kilopascal absolute), preferably from 100 psia to 500 psia (689 to 3447 kilopascal absolute), and a residence time in the range from 1 to 220 minutes, preferably from 20 to 200 minutes, such as from 100 to 200 minutes. Such conditions are optimized to favor the dimerization reaction between CPD molecules and to minimize the reactions between CPD and other diolefins.

From the reactor 139, a second reactor effluent 141 comprising CPD, other C5 hydrocarbons, and DCPD is then fed into a second separation device 143 (SD2), which can be a distillation column. From column 143, an ultra high-purity DCPD lower stream 147 and an upper stream comprising CPD and other C5 hydrocarbons are obtained. Stream 147 can comprise DCPD at a concentration of at least 95 wt %, such as 96 wt %, 98 wt %, 99 wt %, or even higher, based on the total weight of the C10 hydrocarbons of the stream 147. Stream 147 may be purified in a subsequent distillation column (not shown) to obtain (1) an ultra high-purity DCPD, which comprises DCPD at a concentration of at least 95 wt %, such as 96 wt %, 98 wt %, 99 wt %, or even higher, based on the total weight of the stream; (2) a light wash oil-rich stream, which can be recycled to vessel 163 and/or washing vessel 123 described above (not shown).

Upper stream 145, which is the second C5-rich fraction in the process of the present invention, is then fed into a second dimerization reactor (the third reactor of the present invention, R3) 149 operated under a second set of dimerization conditions, where the remaining CPD in stream 147 is partly converted into DCPD. The second set of dimerization conditions advantageously comprise: a temperature in the range from 30 to 250° C., preferably from 100 to 140° C., and a total absolute pressure in the range from 50 psia to 1000 psia (345 to 6895 kilopascal absolute), preferably from 100 psia to 500 psia (689 to 3447 kilopascal absolute), and a residence time in the range from 1 to 300 minutes, preferably from 150 to 300 minutes. Such conditions are optimized to maximize recovery of the remaining CPD while achieving on-spec production of a subsequent DCPD fraction.

From the reactor 149, a third reactor effluent 151 comprising CPD, other C5 hydrocarbons, and DCPD is then fed into a third separation device 153 (SD3), which can be a distillation column. From column 153, a high-purity DCPD lower stream 155 and an upper stream comprising CPD and other C5 hydrocarbons 157 are obtained. Stream 155 can comprise DCPD at a concentration of at least 90 wt %, such as 92 wt %, 94 wt %, 95 wt %, or even higher, based on the total weight of the C10 hydrocarbons of the stream 155. Stream 155 may be purified in a subsequent distillation column (not shown) to obtain (1) a high-purity DCPD, which comprises DCPD at a concentration of at least 90 wt %, such as 92 wt %, 94 wt %, 95 wt %, or even higher, based on the total weight of the stream; (2) a light wash oil-rich stream, which can be recycled to vessel 163 and/or washing vessel 123 described above (not shown).

DCPD streams 147 and 155 may be sold or delivered as products. The user may convert these streams back into CPD or other compounds, depending on the intended applications.

Upper stream 157, which is the third C5-rich fraction in the process of the present invention, can be fed into a third dimerization reactor (not shown), where the remaining CPD therein can be converted into an additional amount of DCPD, which can be separated and recovered as a third DCPD-rich fraction in a fourth separation device (not shown), if so desired. If a third dimerization reactor is utilized, the preferred modes of operation for the first dimerization reactor and second dimerization reactor can be advantageously adjusted for the purpose of producing DCPD products at optimal quality levels, each with optimal quantities. Typically, the third DCPD-rich fraction would have a lower purity than the first and second DCPD-rich fractions produced upstream in the process as described above.

As shown in FIG. 1, the third C5-rich fraction stream 157 from the third separation device 153 is divided into two streams 159 and 161. To the extent streams 157, 159, and 161 may comprise C6+ in addition to C5 hydrocarbons, stream 161 is then separated in distillation column 163 to obtain a fifth C5-rich stream 165 that is depleted with C6+ and a C6-rich stream 167. Stream 165 can then be recycled to the first reactor 113 (R1) as stream 109, as described above. Stream 167 may be purged or used in other applications, such as an untreated mogas component as described below. It has been found that in this particular embodiment, without the distillation column 163, if the weight ratio of stream 161 to stream 159 is higher than 0.4:0.6, accumulation of C6+ species may occur in the system. It is highly desired that stream 161 is subjected to purification in column 163 before being recycled to the first reactor to eliminate such restriction on the recycle ratio.

Stream 159 (and, optionally, a portion of the first C5-rich fraction stream 137, and a portion of the second C5-rich fraction stream 145, not shown in FIG. 1) can be used for many purposes, due to the many useful components contained therein: CPD, cyclopentane, cyclopentene, pentene, pentadiene, 2-methylbutadiene, and the like.

For example, stream 159 (and other C5-rich fraction streams, and C6-rich stream 167) can be partly or entirely converted into a mogas component by selective hydrogenation to convert at least a portion of the dienes therein to mono olefins and/or saturates. The high concentrations of cyclopentane and cyclopentene in stream 159 after hydrogenation makes it particularly suitable for mogas blending due to the high octane and lower Reid Vapor Pressure values of cyclopentane and cyclopentene relative to the starting feedstock of acyclic C5 hydrocarbon such as n-pentane. The C6-rich stream 167 may be used directly as a mogas component after selective hydrogenation as well.

For another example, before or after selective hydrogenation, stream 159 (and other C5-rich fraction streams) may be separated to obtain at least one pure stream of the following: cyclopentane, cyclopentene, pentene, 1,3-pentadiene, 1,4-pentadiene, and 2-methylbutadiene.

Figure 2:
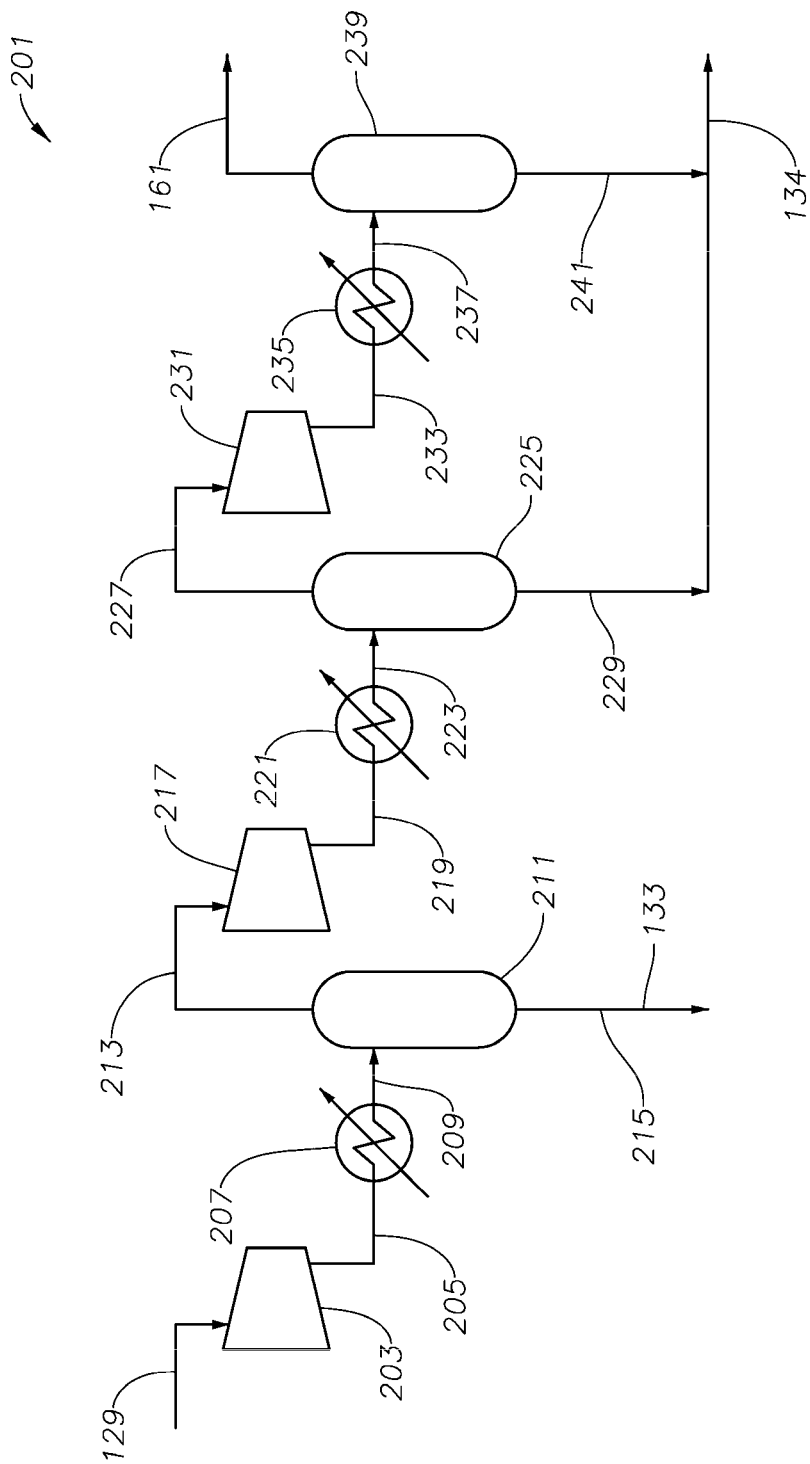
FIG. 2 is a schematic illustration of the details of the first separation sub-system in FIG. 1.

FIG. 2 schematically illustrates an exemplary first separation sub-system 201 useful in the process and system of the present invention, particularly in the exemplary process illustrated in FIG. 1. The first separation sub-system 201 in FIG. 2 comprises a compression train including multiple-stage compression, cooling and liquid/vapor separation. In the process of this figure, the upper stream 129, comprising a majority of cleaned first reactor effluent obtained from column 123, is first fed into a first-stage compressor 203, from which a stream 205 at a higher pressure is obtained. Stream 205 is then cooled by a first-stage heat exchanger 207 to obtain a liquid/vapor mixture stream 209, which is fed into a first-stage liquid/vapor separation device (such as a drum) 211 to obtain a first-stage lower liquid stream 215 comprising C5 hydrocarbons, but depleted of hydrogen and C1-C4 hydrocarbons and a first-stage upper vapor stream 213 comprising C5 hydrocarbons and rich in hydrogen and C1-C4 hydrocarbons. Stream 213 is then compressed by a second-stage compressor 217 to obtain a stream 219 with an even higher pressure, which is then cooled by a second-stage heat exchanger 221 to obtain a second-stage lower temperature liquid/vapor mixture stream 223, which is separated in a second-stage liquid/vapor separation device (such as a drum) 225 to obtain a second-stage lower liquid stream 229 comprising C5 hydrocarbons, but depleted of hydrogen and C1-C4 hydrocarbons and a second-stage vapor stream 227 comprising C5 hydrocarbons and rich in hydrogen and C1-C4 hydrocarbons. Stream 227 is then compressed by a third-stage compressor 231 to obtain a stream 233 with an even higher pressure, which is then cooled by a third-stage heat exchanger 235 to obtain a lower temperature third-stage liquid/vapor mixture stream 237, which is separated in a third-stage liquid/vapor separation device (such as a drum) 239 to obtain a third-stage lower liquid stream 241 comprising C5 hydrocarbons, but depleted of hydrogen and C1-C4 hydrocarbons and a third-stage upper vapor stream 161 comprising rich in hydrogen and C1-C4 hydrocarbons and, optionally, comprising C5 hydrocarbons at a lower concentration. Stream 161 is then fed to a vessel 163 as illustrated in FIG. 1 and described above.

As shown in FIG. 2, stream 215, to the extent it may comprise non-negligible concentrations of at least one of the wash oil, C7 and C8+(such as DCPD), can be fed into the heavy wash oil-removal column 135 together with stream 127, where it is processed to obtain a C5-rich stream 137, depleted with heavy wash oil as described above in connection with FIG. 1. Downstream streams 229 and 241, to the extent they tend to comprise lower concentrations, if any at all, of the heavy wash oil, C7 and C8+, may be combined to form a single stream 134, which is then combined with stream 137 as the first C5-rich fraction directly fed into the first dimerization reactor 139 (R2) as illustrated in FIG. 1.

It is contemplated, though not shown, that streams 215, 229, and 241, to the extent they may all contain non-negligible concentrations of at least one of the heavy wash oil, C7 and C8+(such as DCPD), may be all delivered to the heavy wash oil-removal column 135 along with stream 127, where the C5-rich stream 137 is obtained and delivered to the first dimerization reactor 139.

It is also contemplated, though not shown, that streams 215, 229, and 241, to the extent they may all contain the heavy wash oil, C7 and C8+ at sufficiently low concentrations, if any at all, may be combined with stream 137 and then delivered directly to the first dimerization reactor 139.

INDUSTRIAL APPLICABILITY

The first hydrocarbon reactor effluent obtained during the acyclic C5 conversion process containing cyclic, branched, and linear C5 hydrocarbons and, optionally, containing any combination of hydrogen, C4 and lighter byproducts, or C6 and heavier byproducts is a valuable product in and of itself. Preferably, CPD and/or DCPD may be separated from the reactor effluent to obtain purified product streams, which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

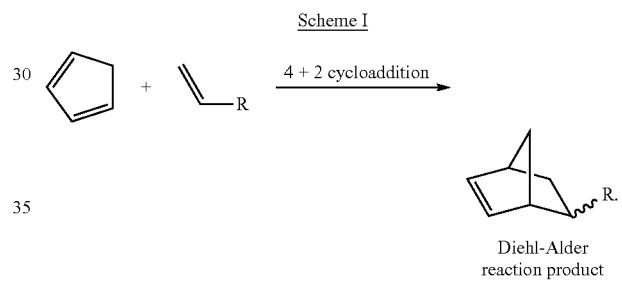

where R is a heteroatom or substituted heteroatom, substituted or unsubstituted C1-C50 hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the monoolefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins and substituted versions of the foregoing. Preferred Diels-Alder reaction products include norbornene, ethylidene norbornene, substituted norbornenes (including oxygen containing norbornenes), norbornadienes, and tetracyclododecene, as illustrated in the following structures:

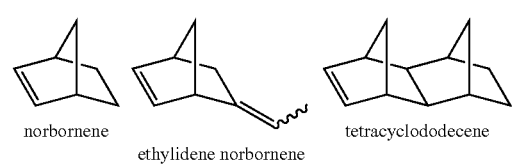

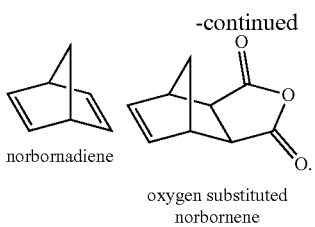

norbornadiene     oxygen substituted norbornene

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

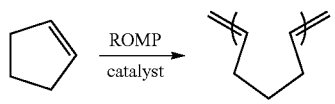

Separated cyclopentane is useful as a blowing agent and as a solvent. Linear and branched $C_5$ products are useful for conversion to higher olefins and alcohols. Cyclic and non cyclic $C_5$ products, optionally after hydrogenation, are useful as octane enhancers and transportation fuel blend components.

EXAMPLES

The following non-limiting examples 1-11 illustrate the invention. Examples 1-9 are obtained by using simulation. In Examples 1-3, the respective first reactor hydrocarbon effluents are fed forward to the quench/wash section (123), a compression train section (SD1, 131), and a debutanization section (163) in similar manners as discussed above. All the recovered C5-rich fractions produced from the quench/wash section (135), the compression train section (SD1, 131), and debutanization section (163) are routed to the heavy wash oil removal column (135), and subsequently to a first dimerization reactor (R2, 139), an ultra high-purity DCPD recovery column (SD2, 143), a second dimerization reactor (R3, 149), and then a high-purity DCPD recovery column (SD3, 153). Examples 4-9 are simulation results of eductor systems operating under various eductor conditions that may be useful in various embodiments of the process of the present invention.

Example 1

In this example, a first reactor effluent produced from pure n-pentane feedstock, a pure hydrogen co-feedstock with 1:2 hydrogen/n-pentane molar ratio, without co-feeding a light hydrocarbon or recycling of any down-stream C5-rich fractions to the first reactor. The process temperature, pressure, and molecular weight at the reactor inlet are 475° C., 62 psia (401.9 kilopascal absolute), and 49.01 g/mol, respectively. Temperature and pressure at the reactor outlet are 575° C. and 10 psia (68.9 kilopascal absolute), respectively. The reactions generate an additional 1.87 moles of molecules in the first reactor effluent exiting the outlet per mole of molecules in the total feed material at the inlet. This 1.87-fold molar expansion has the effects of lowering the molecular weight and density of the stream mixture from 49.01 g/mol at the inlet to 27.05 g/mol at the outlet and from 3.08 kg/m³ at the inlet to 0.26 kg/m³ at the outlet, respectively. The pressure drop from the inlet to the outlet of the first reactor is calculated to be about 52 psi (359 kilopascal). Composition of the first reactor effluent at the outlet is given in Table I below.

The entire third C5-rich fraction is used as a mogas blend for making mogas, the composition of the mogas blend is provided in Table I below as well.

In this example, to produce 100 tons of CPD in stream 117, a total weight of 403 tons of n-pentane feed is fed to the system (representing a total CPD yield of 24.8 wt %, based on all weight of the n-pentane feed), a total weight of 13.1 tons of hydrogen is produced, a total weight of 82 tons of UHP DCPD with purity level exceeding 99.0 wt % (stream 147) is produced, a total weight of 11 tons of DCPD with purity level exceeding 90.0 wt % (stream 155) is produced, and a total weight of 238 tons of mogas blend is produced.

Example 2

The reactor inlet and outlet temperature and pressure remain the same as in Example 1 above. However, in this example, a C5-rich stream, produced as 35% of the third C5-rich fraction obtained by separating the third reactor effluent produced from a second dimerization reactor described above, is recycled to the first reactor, where it is admixed with n-pentane before being fed into the first reactor. Hydrogen is co-fed at $H_2$/(all C5 hydrocarbons except (iso-C5 hydrocarbons and CPD)) molar ratio of 1:2. It has been experimentally found that the reaction pathway from iso-C5 hydrocarbons to CPD is kinetically inhibited under the reaction conditions. The composition of the total feed to the first reactor is given in Table I below.

The remaining 65% of the third C5-rich fraction is used as a mogas blend for making mogas. The composition of the mogas blend is provided in Table I below as well.

In this example, to produce 100 tons of CPD in stream 117, a total weight of 308 tons of n-pentane feed is fed into the system (representing a CPD yield of 32.5 wt %, based on the total weight of the n-pentane feed), a total weight of 11.7 tons of hydrogen is produced, a total weight of 85 tons of UHP DCPD (stream 147) with purity level exceeding 99.0 wt % is produced, a total weight of 8 tons of DCPD (stream 155) with purity level exceeding 90.0 wt % is produced, and a total weight of 146 tons of mogas blend is produced.

To produce the same amount of CPD, Example 2 (with 35% recycle of the third C5-rich fraction to the first reactor) requires 23.4% less of fresh n-pentane feed than Example 1 (without recycle of any of the C5-rich fraction to the first reactor).

To produce the same amount of CPD, Example 2 produces 10.8% less of hydrogen than Example 1, due to using partially unsaturated feed versus a fully saturated feed. This has the benefit of reduced volumetric flow rates in the reactor(s) and downstream equipment. For example, the first reactor in Example 2 shows a 7.8% reduction in volumetric flow than in Example 1. This may have significant impacts on the equipment sizing of the downstream quench tower(s), gas compressor(s), and debutanizer(s).

The enthalpy changes of the stream across the first reactor also shows significant reduction in Example 2 compared to Example 1. This translates into a 10.9% reduction in furnace firing in Example 2, which can have a significant impact of the equipment sizing of the reactor(s) and fuel costs. The amount of heat required for sustaining the endothermic reactions in the first reactor is comparatively lower when using a partially converted C5 feedstock.

To produce 100 tons of CPD, Example 2 shows a 38.6 wt % of reduction of materials diverted to mogas production. Furthermore, it can be seen from Table I that the mogas stream in Example 2 has a slightly higher octane value of C5+ byproduct than in Example 1 since more kinetically limited isomerization and aromatization products will be concentrated into a smaller byproduct stream.

Thus, clearly, it may be advantageous to recycle at least part of the C5-containing streams to the CPD reactor(s). This is especially beneficial if demand for the partially converted C5 hydrocarbons is reduced, e.g., during certain seasons when the RVP spec on mogas limits the amount of C5 hydrocarbons that can be blended. This allows the plant to continue to operate at desired DCPD product rates with lower quantities of co-products.

TABLE I

| Component | Total Feed Composition (wt %) Example | | Composition of First Reactor Hydrocarbon Effluent at Exit (wt %) Example | | Composition of Mogas Blend (wt %) Example | |
|---|---|---|---|---|---|---|
| | 1 | 2 | 1 | 2 | 1 | 2 |
| Hydrogen | 1.30 | 1.30 | 4.51 | 4.28 | — | — |
| Methane | 0.00 | 0.00 | 1.50 | 1.34 | — | — |
| Ethylene | 0.00 | 0.00 | 0.11 | 0.10 | — | — |
| Ethane | 0.00 | 0.01 | 0.97 | 0.87 | — | — |
| Propylene | 0.00 | 0.04 | 0.73 | 0.70 | 0.04 | 0.07 |
| Propane | 0.00 | 0.06 | 0.75 | 0.72 | 0.05 | 0.08 |
| Isobutane | 0.00 | 0.00 | 0.00 | 0.00 | 0.00 | 0.00 |
| Isobutylene | 0.00 | 0.03 | 0.14 | 0.16 | 0.03 | 0.05 |
| 1-butene | 0.00 | 0.18 | 0.73 | 0.82 | 0.14 | 0.27 |
| 1,3-butadiene | 0.00 | 0.05 | 0.19 | 0.22 | 0.04 | 0.07 |
| n-butane | 0.00 | 0.22 | 0.79 | 0.93 | 0.17 | 0.33 |
| t-2-butene | 0.00 | 0.23 | 0.80 | 0.94 | 0.18 | 0.35 |
| c-2-butene | 0.00 | 0.18 | 0.58 | 0.70 | 0.13 | 0.27 |
| 3-methyl-1-butene | 0.00 | 0.02 | 0.05 | 0.06 | 0.01 | 0.03 |
| 1,4-pentadiene | 0.00 | 0.02 | 0.05 | 0.05 | 0.01 | 0.02 |
| Isopentane | 0.00 | 0.10 | 0.22 | 0.30 | 0.06 | 0.14 |
| 1-pentene | 0.00 | 1.28 | 3.99 | 3.98 | 1.19 | 1.95 |
| 2-methyl-1-butene | 0.00 | 0.09 | 0.19 | 0.26 | 0.06 | 0.13 |
| Isoprene | 0.00 | 0.02 | 0.06 | 0.08 | 0.01 | 0.03 |
| n-pentane | 98.70 | 88.73 | 32.64 | 30.87 | 9.81 | 15.27 |
| t-2-pentene | 0.00 | 2.51 | 7.72 | 7.67 | 2.34 | 3.81 |
| c-2-pentene | 0.00 | 1.41 | 4.35 | 4.31 | 1.32 | 2.14 |
| 2-methyl-2-butene | 0.00 | 0.15 | 0.33 | 0.46 | 0.10 | 0.23 |
| CPD | 0.00 | 0.17 | 24.51 | 25.57 | 0.08 | 0.25 |
| t-1,3-pentadiene | 0.00 | 0.91 | 2.78 | 2.81 | 0.82 | 1.38 |
| c-1,3-pentadiene | 0.00 | 0.74 | 2.28 | 2.32 | 0.67 | 1.12 |
| Cyclopentene | 0.00 | 1.14 | 3.43 | 3.51 | 1.03 | 1.73 |
| Cyclopentane | 0.00 | 0.18 | 0.56 | 0.56 | 0.17 | 0.27 |
| Benzene | 0.00 | 0.25 | 0.72 | 0.89 | 0.19 | 0.37 |
| Toluene | 0.00 | 0.00 | 0.00 | 0.00 | — | — |

TABLE I-continued

| Component | Total Feed Composition (wt %) Example | | Composition of First Reactor Hydrocarbon Effluent at Exit (wt %) Example | | Composition of Mogas Blend (wt %) Example | |
|---|---|---|---|---|---|---|
| | 1 | 2 | 1 | 2 | 1 | 2 |
| Meta-xylene | 0.00 | 0.00 | 0.00 | 0.00 | — | — |
| DCPD | 0.00 | 0.00 | 0.00 | 0.00 | — | — |
| Di-isoprene | 0.00 | 0.00 | 0.00 | 0.00 | — | — |
| Naphthalene | 0.00 | 0.00 | 2.45 | 2.55 | — | — |
| Methylnaphthalene | 0.00 | 0.000 | 0.00 | 0.00 | — | — |
| Anthracene | 0.00 | 0.00 | 1.70 | 1.77 | — | — |
| Pyrene | 0.00 | 0.00 | 0.19 | 0.20 | — | — |
| TOTAL | 100.00 | 100.00 | 100.00 | 100.00 | 100.00 | 100.00 |

Example 3

In this prophetic example, obtained by simulation, a model third C5-rich fraction used as the mogas blend and a corresponding partially hydrogenated mogas component having the following compositions in Table II can be obtained:

TABLE II

| | Concentration in (wt %) | |
|---|---|---|
| Components | Third C5-rich Fraction | Post-Selective Hydrogenation |
| Propylene | 0.22 | 0.22 |
| Propane | 0.27 | 0.27 |
| Isobutane | 0.00 | 0.00 |
| Isobutylene | 0.14 | 0.14 |
| 1-butene | 0.75 | 0.81 |
| 1,3-butadiene | 0.21 | 0.00 |
| n-butane | 0.91 | 0.91 |
| t-2-butene | 0.95 | 1.01 |
| c-2-butene | 0.72 | 0.79 |
| 3-methyl-1-butene | 0.07 | 0.07 |
| 1,4-pentadiene | 0.07 | 0.00 |
| Isopentane | 0.34 | 0.34 |
| 1-pentene | 6.36 | 9.11 |
| 2-methyl-1-butene | 0.30 | 0.32 |
| Isoprene | 0.05 | 0.00 |
| n-pentane | 52.59 | 52.59 |
| t-2-pentene | 12.54 | 15.21 |
| c-2-pentene | 7.08 | 9.75 |
| 2-methyl-2-butene | 0.54 | 0.56 |
| Cyclopentadiene | 0.44 | 0.00 |
| t-1,3-pentadiene | 4.41 | 0.00 |
| c-1,3-pentadiene | 3.61 | 0.00 |
| Cyclopentene | 5.54 | 5.98 |
| Cyclopentane | 0.90 | 0.90 |
| Benzene | 1.01 | 1.01 |
| C10 (dimers) | 0.00 | 0.00 |
| Total | 100.00 | 100.00 |

Examples 4-9: Using Eductors

The reactor outlet conditions of 575° C. and 8 psia (55 kilopascal absolute) are used in the following Examples 4-9. If a higher outlet pressure of 16 psia (110 kilopascal absolute) was used, the CPD yield would be decreased by as much as 43%. If an eductor was instead used to increase the pressure at the outlet from 8 psia (55 kilopascal) to 16 psia (110 kilopascal) (in order to prevent air/oxygen ingress to downstream equipment), no yield debits would be expected.

The following Examples 4-9 use an eductor to process a first reactor hydrocarbon effluent having a molecular weight of 27.1 g/mol and first reactor outlet temperature of 575° C. These examples are used to demonstrate the technical feasibility of an advantaged process to rapidly compress, quench, and dilute the reactor effluent with the aid of intense mixing with high-pressure motive fluids using the eductor system. The eductor has a suction pressure of 8 psia (55 kilopascal absolute). The eductor effluent at the exit has an overall pressure of 16 psia (110 kilopascal absolute). Various motive fluids at various pressure and temperatures can be used under various eductor conditions. Eductor operation conditions and results are shown in Table III below. The amount of motive fluid required can be reduced by increasing the motive fluid pressure and/or temperature. As can be clearly seen from the data in Table III, compared to the first reactor hydrocarbon effluent at the reactor outlet, the eductor effluent have increased overall pressures and decreased temperatures—both desirable for downstream separation operations.

synthesized crystals were converted (for characterization) into the hydrogen form by three ion exchanges with ammonium nitrate solution at room temperature, followed by drying at 250° F. (121° C.) and calcination at 1000° F. (540° C.) for 6 hours. The resulting ZSM-5 crystals had a $SiO_2$/$Al_2O_3$ molar ratio of ~414, total surface area (SA)/(micropore SA+ mesopore SA) of 490 (440+51) $m^2$/g, Hexane sorption of 117 mg/g and an Alpha value (as measured on the proton form) of 31. A second portion of the material was used as synthesized for Pt impregnation.

ZSM-5 having a $SiO_2$/$Al_2O_3$ molar ratio of 414 and a sodium content of 0.38 wt % was calcined for 6 hours in nitrogen at 900° F. (482° C.). After cooling, the sample was reheated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, 0.5 wt % Pt was added via incipient wetness impregnation using an aqueous solution of tetraamine platinum hydroxide. The catalyst composition was

TABLE III

| | | Example | | | | | |
|---|---|---|---|---|---|---|---|
| | | 4 | 5 | 6 | 7 | 8 | 9 |
| First reactor hydrocarbon effluent | Molecular weight (g/mol) | 27.1 | 27.1 | 27.1 | 27.1 | 27.1 | 27.1 |
| | Outlet temperature (° C.) | 575 | 575 | 575 | 575 | 575 | 575 |
| Motive Fluid | Material | Saturated steam | Saturated toluene vapor | Saturated toluene vapor | Methane | Methane | Methane |
| | Temperature (° C.) | 194 | 237 | 287 | 30 | 300 | 475 |
| | Pressure (kilopascal) | 1379 | 1379 | 2758 | 1379 | 1379 | 499 |
| | Ratio of motive fluid mass flow to first reactor hydrocarbon effluent mass flow | 1.24 | 2.38 | 1.51 | 1.29 | 0.93 | 1.02 |
| Eductor conditions | Suction pressure (kilopascal) | 55 | 55 | 55 | 55 | 55 | 55 |
| | Expansion ratio | 25 | 25 | 50 | 25 | 25 | 9.1 |
| | Compression ratio | 2 | 2 | 2 | 2 | 2 | 2 |
| Eductor Effluent | Temperature (° C.) | 418 | 377 | 435 | 300 | 444 | 523 |
| | Pressure (kilopascal) | 110 | 110 | 110 | 110 | 110 | 110 |

Example 10—ZSM-5 Catalyst Composition Synthesis

A synthesis mixture with ~20.3% solids was prepared from 10,000 g of deionized (DI) water, 600 g of 50% NaOH solution, 25 g of 45% Sodium Aluminate solution, 730 g of n-propyl amine 100% solution, 80 g of ZSM-5 seed crystals, and 3,190 g of Ultrasil PM™. Modified silica were mixed in a 5-gal pail container and then charged into a 5-gal autoclave after mixing. The synthesis mixture had the following molar composition:

| | |
|---|---|
| $SiO_2$/$Al_2O_3$ | ~470 |
| $H_2O$/$SiO_2$ | ~12.1 |
| OH/$SiO_2$ | ~0.16 |
| Na/$SiO_2$ | ~0.16 |
| n-PA/Si | ~0.25 |

The synthesis mixture was mixed and reacted at 230° F. (110° C.) at 250 rpm for 72 hours. The resulting product was filtered and washed with DI water and then dried in the oven at ~250° F. (121° C.) overnight. A portion of the asdried in air at room temperature for 2 hours, then at 250° F. (121° C.) for 4 hours, and lastly calcined in air at 660° F. (349° C.) for 3 hours. The catalyst composition powder was pressed (15 ton), crushed, and sieved to obtain 20-40 mesh particle size.

Example 11—Catalyst Composition Performance Evaluation

The above material of Example 10 was evaluated for performance. The catalyst composition (0.5 g) was physically mixed with quartz (1.5 g, 60-80 mesh) and loaded into a reactor. The catalyst composition was dried for 1 hour under He (100 mL/min, 30 psig (207 kPa), 250° C.) then reduced for 1 hour under $H_2$ (200 mL/min, 30 psig (207 kPa), 500° C.). The catalyst composition was then tested for performance with feed of n-pentane, $H_2$, and balance He, typically at 550° C.-600° C., 5.0 psia (35 kPa-a) $C_5H_{12}$, 1.0 molar $H_2$:$C_5H_{12}$, 14.7 $h^{-1}$ WHSV, and 30 psig (207 kPa) total. Catalyst composition stability and regenerability was tested post initial tests at 550° C. to 600° C. by treatment with $H_2$ (200 mL/min, 30 psig (207 kPa), 650° C.) for 5 hours, then retesting performance at 600° C.

Cyclopentadiene and three equivalents of hydrogen are produced by dehydrogenation and cyclization of n-pentane (Equation 1). This is achieved by flowing n-pentane over a solid-state, Pt containing catalyst composition at elevated temperature. The performance of ZSM-5(414:1)/0.5% Pt of Example 10 was evaluated based on n-pentane conversion, cyclic C5 production (cC5), cracking yields, and stability. These results are summarized in Table V, Table VI, Table VII, and Table VIII.

$$C_5H_{12} \xrightarrow{\Delta} C_5H_6 + 3H_2 \quad \text{Equation (1)}$$

H2:C5, 14.7 WHSV, 45 psia (310 kPa-a) total. In Table V, the selectivities and yields are expressed on a molar percentage basis for the respective cyclic C5, CPD, iso-C5, C1, and C2-4 of hydrocarbons formed; i.e., the molar selectivity is the moles of the respective cyclic C5, CPD, C1, and C2-4 formed divided by total moles of pentane converted. In Table VII, the selectivities and yields are expressed on a carbon percentage basis for the respective cyclic C5, CPD, iso-C5, C1, and C2-4 of hydrocarbons formed; i.e., the carbon selectivity is the moles carbon in the respective cyclic C5, CPD, iso-C5, C1, and C2-4 formed divided by total moles of carbon in the pentane converted. As can be seen, Table V and Table VII show greater than 80% conversion of pentane, at high WHSV, and 40% selectivity to

TABLE V

| Temperature | Conversion (%) | Selectivity (mol %) | | | | | Yield (mol %) | | | | | |
|---|---|---|---|---|---|---|---|---|---|---|---|---|
| (° C.) | C5H12 | cC5 | CPD | C1 | C2-4 | iC5 | cC5 | CPD | C1 | C2-4 | iC5 | cC5:C1-4 |
| 545 | 71 | 33 | 20 | 11 | 21 | 4.4 | 24 | 14 | 8.1 | 15 | 3.1 | 1.0 |
| 570 | 80 | 37 | 26 | 13 | 22 | 3.7 | 30 | 21 | 10 | 17 | 3.0 | 1.1 |
| 595 | 84 | 40 | 32 | 13 | 22 | 3.1 | 34 | 26 | 11 | 18 | 2.6 | 1.1 |
| 595, Post H2 | 76 | 38 | 30 | 16 | 22 | 2.4 | 29 | 23 | 12 | 17 | 1.8 | 1.0 |

TABLE VI

| Temperature | Conversion (%) | Selectivity (mol %) | | | | Yield (mol %) | | | |
|---|---|---|---|---|---|---|---|---|---|
| (° C.) | C5H12 | iC5 | iC5o | iC5= | iC5== | iC5 | iC5o | iC5= | iC5== |
| 545 | 71 | 4.4 | 1.1 | 3.2 | 0.04 | 3.1 | 0.8 | 2.3 | 0.03 |
| 570 | 80 | 3.7 | 0.8 | 2.8 | 0.05 | 3.0 | 0.7 | 2.3 | 0.04 |
| 595 | 84 | 3.1 | 0.7 | 2.4 | 0.05 | 2.6 | 0.6 | 2.0 | 0.05 |
| 595, Post H2 | 76 | 2.4 | 0.6 | 1.8 | 0.04 | 1.8 | 0.5 | 1.4 | 0.03 |

TABLE VII

| Temperature | Conversion (%) | Selectivity (C %) | | | | | Yield (C %) | | | | | |
|---|---|---|---|---|---|---|---|---|---|---|---|---|
| (° C.) | C5H12 | cC5 | CPD | C1 | C2-4 | iC5 | cC5 | CPD | C1 | C2-4 | iC5 | cC5:C1-4 |
| 545 | 71 | 40 | 24 | 2.8 | 15 | 5.3 | 28 | 17 | 2.0 | 11 | 3.7 | 2.2 |
| 570 | 80 | 45 | 32 | 3.1 | 16 | 4.5 | 36 | 26 | 2.5 | 13 | 3.6 | 2.3 |
| 595 | 84 | 50 | 39 | 3.3 | 16 | 3.8 | 42 | 33 | 2.8 | 14 | 3.2 | 2.5 |
| 595, Post H2 | 76 | 48 | 38 | 4.1 | 17 | 3.0 | 37 | 29 | 3.1 | 13 | 2.3 | 2.3 |

TABLE VIII

| Temperature | Conversion (%) | Selectivity (C %) | | | | Yield (C %) | | | |
|---|---|---|---|---|---|---|---|---|---|
| (° C.) | C5H12 | iC5 | iC5o | iC5= | iC5== | iC5 | iC5o | iC5= | iC5== |
| 545 | 71 | 5.3 | 1.4 | 3.8 | 0.05 | 3.7 | 1.0 | 2.7 | 0.04 |
| 570 | 80 | 4.5 | 1.0 | 3.5 | 0.06 | 3.6 | 0.8 | 2.8 | 0.04 |
| 595 | 84 | 3.8 | 0.8 | 2.9 | 0.07 | 3.2 | 0.7 | 2.5 | 0.06 |
| 595, Post H2 | 76 | 3.0 | 0.8 | 2.2 | 0.05 | 2.3 | 0.6 | 1.7 | 0.03 |

Table V and Table VII show the conversion of n-pentane and selectivity and yield of cyclic C5, CPD, iso-C5, C1, and C2-4 cracking products at varying temperatures (average values over 8 hours at each temperature) for a catalyst composition of 0.5 g ZSM-5(Si:Al$_2$ molar ratio 414:1)/0.5 wt % Pt at conditions of 5.0 psia (35 kPa-a) C$_5$H$_{12}$, 1:1 molar cyclic C5 species at 595° C. While not the specific end product, cyclopentane and cyclopentene can be recycled to produce CPD.

Tables VI and VIII further specify the individual iC5 components which are shown as totals in Tables V and VII. iC5o is iso pentane; including 2-methyl butane and 3-methyl butane. iC5= is isopentenes including 2-methyl butene and 3-methyl butene. iC5== is iso-pentadienes; including 2-methyl butadiene and 3-methyl butadiene. These results show the low levels of iso-pentadienes that are possible with the example catalyst.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition element, or elements and vice versa.

What is claimed is:

1. A process for making cyclopentadiene (CPD) and/or dicyclopentadiene (DCPD), the process comprising:
   (I) feeding a C5 feedstock comprising at least one acyclic C5 hydrocarbon into a first reactor;
   (II) contacting the at least one acyclic C5 hydrocarbon with a catalyst under conversion conditions to obtain a first reactor hydrocarbon effluent from an outlet of the first reactor comprising: C5 components including CPD and acyclic diolefins; light components including hydrogen and C1-C4 hydrocarbons; one-ring aromatics; and multiple-ring aromatics;
   (III) feeding at least a portion of the first reactor hydrocarbon effluent to a suction chamber of an eductor;
   (IV) injecting a stream of a motive fluid through a nozzle into the suction chamber;
   (V) obtaining an eductor effluent from an exit of the eductor comprising the motive fluid and CPD;
   wherein:
   the overall pressure of the first reactor effluent at the outlet of the first reactor is lower than the overall pressure of the eductor effluent at the exit of the eductor; and
   the temperature of the first reactor effluent at the outlet of the first reactor is higher than the temperature of the eductor effluent at the exit of the eductor.

2. The process of claim 1, further comprising:
   (VI) separating at least a portion of the eductor effluent in a first separation sub-system to obtain (i) a first light components-rich fraction including H2 and C1-C4 hydrocarbons; (ii) a first C5-rich fraction; and (iii) a first multiple-ring aromatics-rich fraction.

3. The process of claim 1, wherein:
   the first reactor hydrocarbon effluent comprises CPD at a concentration of C(CPD)1 wt % and acyclic diolefins at a total concentration of C(ADO)1 wt %, both based on the total weight of C5s in the first reactor hydrocarbon effluent; and
   C(CPD)1/C(ADO)1≥1.5.

4. The process of claim 1, wherein:
   the first reactor effluent at the outlet of the first reactor has an overall pressure in the range from 20 to 100 kilopascal and/or a temperature in the range from 500° C. to 800° C.

5. The process of claim 4, wherein:
   the eductor effluent at the exit of the eductor has an overall pressure in the range from 100 kilopascal to 400 kilopascal and/or a temperature in the range from 30° C. to 700° C.

6. The process of claim 4, wherein:
   the stream of the motive fluid when entering the suction chamber has an overall pressure in the range from 100 to 10,000 kilopascal and/or a temperature in the range from 30° C. to 700° C.

7. The process of claim 1, wherein:
   the eductor is operated under eductor conditions including at least one of: (i) a compression ratio in the range from 1 to 20; (ii) an entrainment ratio in the range from 0.05 to 3, and (iii) an expansion ratio in the range from 5 to 100.

8. The process of claim 1, wherein the motive fluid comprises at least one of: C1-C5 hydrocarbons, benzene, mono or multiple alkyl benzenes, mono or multiple alkyl naphthalenes, water, and mixtures thereof.

9. The process of claim 1, wherein the motive fluid is essentially free of materials capable of undergoing Diels-Alder condensation reactions with CPD.

10. The process of claim 1, wherein hydrogen is co-fed into the first reactor, and the molar ratio of the hydrogen and the C5 feed fed into the first reactor is in a range from 0.1 to 3.0.

11. The process of claim 1, further comprising recycling at least a portion of the hydrogen in the first light components-rich fraction into the first reactor.

12. The process of claim 2, further comprising:
    (VII) separating at least a portion of the first light components-rich fraction by using one or more of a pressure swing process, a rapid cycle pressure swing adsorption process, a cryogenic process, a thermal swing adsorption process, and a membrane separation process to obtain at least one of the following:
    (i) a hydrogen-rich stream comprising at least 95 mol % of hydrogen;
    (ii) a methane-rich stream; and
    (iii) a C2-C4-rich stream.

13. The process of claim 12, wherein at least a portion of the methane-rich stream and/or the C2-C4 rich stream is used as at least a portion of the motive fluid.

14. The process of claim 2, further comprising:
    (VIII) supplying at least a portion of the first C5-rich fraction into a second reactor operating under a first set of dimerization conditions;
    (IX) obtaining a second reactor effluent from in the second reactor comprising CPD and DCPD; and
    (X) separating at least a portion of the second reactor effluent to obtain a first DCPD-rich fraction comprising DCPD and a second C5-rich fraction.

15. The process of claim 2, wherein step (VI) comprises at least one of the following:
    (VIa) cooling the eductor effluent;
    (VIb) increasing the total pressure of the eductor effluent;
    (VIc) washing at least a portion of the eductor effluent with a wash oil;
    (VId) removing light components from the eductor effluent;
    (VIe) removing C6+ components from the eductor effluent; and
    (VIf) removing at least a portion of the motive fluid.

16. The process of claim 2, wherein step (VI) comprises washing the eductor effluent with a wash oil comprising at least one of: cylcohexane; monoalkyl, dialkyl, and trialkyl cyclohexanes; benzene; monoalkyl, dialkyl, and trialkyl benzenes; monoalkyl, dialkyl, trialkyl, and tetraalkyl naphthalenes; other alkylated multiple-ring aromatics, and mixtures and combinations thereof.

17. The process of claim 2, wherein step (VI) comprises removing C4 and lighter components from the eductor effluent using a compression train with inter-stage cooling and vapor/liquid separation.

18. The process of claim 2, further comprising:
(XI) feeding at least a portion of the second C5-rich fraction into a third reactor operating under a second set of dimerization conditions;
(XII) obtaining a third reactor effluent from the third reactor comprising CPD and DCPD; and
(XIII) separating at least a portion of the third reactor effluent to obtain a second DCPD-rich fraction and a third C5-rich fraction.

19. The process of claim 18, further comprising:
(XIV) feeding at least a portion of the third C5-rich fraction into a fourth reactor operating under a third set of dimerization conditions;
(XV) obtaining a fourth reactor effluent comprising CPD and DCPD; and
(XVI) separating at least a portion of the fourth reactor effluent to obtain a third DCPD-rich fraction and a fourth C5-rich fraction.

20. The process of claim 2, further comprising:
(XVII) recycling, directly or indirectly, at least a portion of at least one of the first C5-rich fraction, the second C5-rich fraction, the third C5-rich fraction, and the fourth C5-rich fraction, if produced, to the first reactor.

21. The process of claim 2, further comprising:
(XVIII) selectively hydrogenating at least a portion of at least one of the first C5-rich fraction, the second C5-rich fraction, the third C5-rich fraction, and the fourth C5-rich fraction, if produced, to obtain a mogas component feed; and
(XIX) forming a motor gas blend from the mogas component feed.

22. The process of claim 21, wherein the mogas component feedstock is essentially free of dienes.

23. The process of claim 2, comprising:
(XX) separating at least a portion of at least one of the first C5-rich fraction, the second C5-rich fraction, the third C5-rich fraction, and the fourth C5-rich fraction, if produced, to obtain a C6-rich fraction and a fifth C5-rich fraction depleted in C6+ hydrocarbons;
(XXI) recycling at least a portion of the fifth C5-rich fraction to the first reactor; and
(XXII) optionally selectively hydrogenating at least a portion of the C6-rich fraction to obtain a mogas component feed.

24. The process of claim 2, comprising:
(XXIII) obtaining at least one of: (i) a cyclopentane-rich fraction; (ii) a cyclopentene-rich fraction; (iii) a 1,3-pentadiene-rich fraction; and (iv) a 2-methyl-1,3-butadiene fraction, from at least one of the first C5-rich fraction, the second C5-rich fraction, the third C5-rich fraction, the fourth C5-rich fraction, and the fifth C5-rich fraction, if produced.

* * * * *